United States Patent
Schraga

(10) Patent No.: US 9,307,939 B2
(45) Date of Patent: Apr. 12, 2016

(54) LANCET DEVICE WITH COMBINED TRIGGER AND COCKING MECHANISM

(71) Applicant: Stat Medical Devices, Inc., North Miami Beach, FL (US)

(72) Inventor: Steven Schraga, Surfside, FL (US)

(73) Assignee: STAT MEDICAL DEVICES, INC., North Miami Beach, FL (US)

(*) Notice: Subject to any disclaimer, the term of this patent is extended or adjusted under 35 U.S.C. 154(b) by 86 days.

(21) Appl. No.: 13/902,508

(22) Filed: May 24, 2013

(65) Prior Publication Data

US 2013/0267814 A1  Oct. 10, 2013

Related U.S. Application Data

(63) Continuation of application No. 11/694,132, filed on Mar. 30, 2007, now Pat. No. 8,469,986.

(51) Int. Cl.
*A61B 5/151* (2006.01)
*A61B 5/15* (2006.01)
*A61B 5/145* (2006.01)
*A61B 5/157* (2006.01)

(52) U.S. Cl.
CPC ........... *A61B 5/15113* (2013.01); *A61B 5/1411* (2013.01); *A61B 5/14532* (2013.01); *A61B 5/157* (2013.01)

(58) Field of Classification Search
CPC ........... A61B 5/15113; A61B 5/15111; A61B 5/15107; A61B 5/1411
USPC ............ 606/181–185; 604/22, 110, 117, 131, 604/134–137, 207–211; 600/583
See application file for complete search history.

(56) References Cited

U.S. PATENT DOCUMENTS

| | | | |
|---|---|---|---|
| 676,678 | A | 6/1901 | Ellifrits |
| 1,135,465 | A | 4/1915 | Pollock |
| 2,699,784 | A | 2/1953 | Scarifier |
| 2,848,809 | A | 2/1956 | Crowder |

(Continued)

FOREIGN PATENT DOCUMENTS

| | | |
|---|---|---|
| CA | 523078 | 3/1956 |
| EP | 0061102 | 9/1982 |

(Continued)

OTHER PUBLICATIONS

Sutor et al., "Bleeding from Standardized Skin Punctures: Automated Technic for Recording Time, Intensity, and Pattern of Bleeding", *A.J.C.P.*, vol. 55, pp. 541-549 (May 1971).

*Primary Examiner* — Thomas McEvoy
(74) *Attorney, Agent, or Firm* — Greenblum & Bernstein, P.L.C.

(57) ABSTRACT

Lancet device including a skin engaging end that includes a lancet opening through which a lancet needle may extend, a movably mounted holding member configured to receive a lancet, and a combined triggering and cocking system structured and arranged to move the holding member to a retracted position during a cocking phase and to cause the holding member to move to an extended position during a triggering phase. A method of puncturing a surface of skin using the lancet device includes disposing the skin engaging end against a user's skin and manually activating the combined triggering and cocking system. This Abstract is not intended to define the invention disclosed in the specification, nor intended to limit the scope of the invention in any way.

21 Claims, 32 Drawing Sheets

(56) References Cited

U.S. PATENT DOCUMENTS

| | | |
|---|---|---|
| 2,823,677 A | 2/1958 | Heinm, Jr. |
| 3,030,959 A | 4/1962 | Grunert |
| 3,589,213 A | 6/1971 | Gourley |
| 3,760,809 A | 9/1973 | Campbell, Jr. |
| 4,064,871 A | 12/1977 | Reno |
| 4,139,011 A | 2/1979 | Benoit et al. |
| 4,157,086 A | 6/1979 | Maiorano et al. |
| 4,203,446 A | 5/1980 | Höfert et al. |
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirley et al. |
| 4,553,541 A | 11/1985 | Burns |
| 4,628,929 A | 12/1986 | Intengan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,035,704 A | 7/1991 | Lambert et al. |
| 5,074,872 A | 12/1991 | Brown et al. |
| 5,133,730 A | 7/1992 | Biro et al. |
| 5,147,375 A | 9/1992 | Sullivan et al. |
| 5,196,025 A | 3/1993 | Ranalletta et al. |
| 5,201,324 A | 4/1993 | Swierczek |
| 5,212,879 A | 5/1993 | Biro et al. |
| 5,267,963 A | 12/1993 | Bachynsky |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cusack et al. |
| 5,318,584 A | 6/1994 | Lange et al. |
| 5,324,303 A | 6/1994 | Strong et al. |
| 5,350,392 A | 9/1994 | Purcell et al. |
| 5,356,420 A | 10/1994 | Czernecki et al. |
| 5,366,470 A | 11/1994 | Ramel |
| 5,368,047 A | 11/1994 | Suzuki et al. |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,487,748 A | 1/1996 | Marshall et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 5/1997 | Schraga |
| 5,628,765 A | 5/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,746,761 A | 5/1998 | Turchin |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,954,738 A | 9/1999 | LeVaughn et al. |
| 5,971,941 A | 10/1999 | Simons et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,086,545 A | 7/2000 | Roe et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,161,976 A | 12/2000 | Liu |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | Le Vaughn et al. |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 | 7/2001 | Schraga |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,540,762 B1 | 4/2003 | Bertling |
| 6,558,402 B1 | 5/2003 | Chelak et al. |
| 6,645,219 B2 | 11/2003 | Roe |
| 6,764,496 B2 | 7/2004 | Schraga |
| 6,793,633 B2 | 9/2004 | Douglas et al. |
| 6,811,557 B2 | 11/2004 | Schraga |
| 6,887,253 B2 | 5/2005 | Schraga |
| 6,918,918 B1 | 7/2005 | Schraga |
| 6,949,111 B2 | 9/2005 | Schraga |
| 6,958,072 B2 | 10/2005 | Schraga |
| 7,087,068 B1 | 8/2006 | Marshall et al. |
| 7,175,641 B1 | 2/2007 | Schraga |
| 7,299,081 B2 | 11/2007 | Mace et al. |
| 7,311,718 B2 | 12/2007 | Schraga |
| 8,469,986 B2 | 6/2013 | Schraga |
| 2001/0027327 A1 | 10/2001 | Schraga |
| 2001/0039387 A1 | 11/2001 | Rutynowski et al. |
| 2002/0077650 A1 | 6/2002 | Schraga |
| 2003/0050655 A1 | 3/2003 | Roe |
| 2003/0050656 A1 | 3/2003 | Schraga |
| 2003/0083686 A1 | 5/2003 | Freeman et al. |
| 2003/0187470 A1 | 10/2003 | Chelak et al. |
| 2003/0199912 A1 | 10/2003 | Pugh |
| 2004/0092995 A1 | 5/2004 | Boecker et al. |
| 2004/0230216 A1 | 11/2004 | LeVaughn et al. |
| 2004/0236251 A1 | 11/2004 | Roe et al. |
| 2004/0260326 A1 | 12/2004 | Lipoma et al. |
| 2004/0267300 A1 | 12/2004 | Mace |
| 2005/0011759 A1 | 1/2005 | Moerman et al. |
| 2005/0038465 A1 | 2/2005 | Shraga |
| 2005/0118071 A1 | 6/2005 | Sacherer |

(56) References Cited

U.S. PATENT DOCUMENTS

| | | |
|---|---|---|
| 2005/0234495 A1 | 10/2005 | Schraga |
| 2005/0240119 A1 | 10/2005 | Draudt et al. |
| 2005/0267505 A9 | 12/2005 | Shraga |
| 2005/0277850 A1 | 12/2005 | Mace et al. |
| 2006/0116705 A1 | 6/2006 | Schraga |
| 2006/0173478 A1 | 8/2006 | Schraga |
| 2006/0224172 A1 | 10/2006 | LeVaughn et al. |
| 2006/0241668 A1 | 10/2006 | Schraga |
| 2007/0083222 A1 | 4/2007 | Schraga |
| 2008/0033468 A1 | 2/2008 | Lathrop et al. |
| 2008/0039885 A1 | 2/2008 | Purcell |
| 2009/0118753 A1 | 5/2009 | Dicesare et al. |

FOREIGN PATENT DOCUMENTS

| | | |
|---|---|---|
| EP | 0137975 | 4/1985 |
| EP | 0189117 | 7/1986 |
| EP | 0 838 195 | 4/1998 |
| EP | 0885590 | 12/1998 |
| EP | 0904731 | 3/1999 |
| EP | 1074219 | 2/2001 |
| EP | 1 142 534 | 10/2001 |
| FR | 1126718 | 11/1956 |
| KR | 10-2001-0020623 | 3/2001 |
| WO | WO 93/19671 | 10/1993 |
| WO | WO 99/63897 | 12/1999 |
| WO | WO 03/022130 | 3/2003 |
| WO | WO 2005/018710 | 3/2005 |

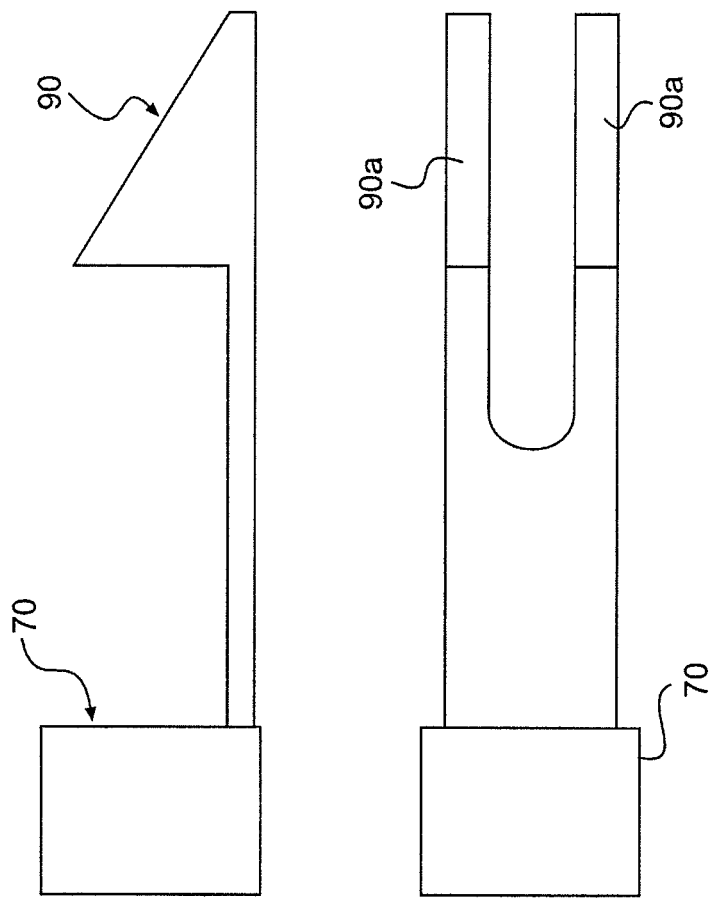

LANCET DEVICE WITH COMBINED TRIGGER AND COCKING MECHANISM

CROSS-REFERENCE TO RELATED APPLICATIONS

This application is a continuation of U.S. application Ser. No. 11/694,132 filed Mar. 30, 2007, the disclosure of this application is incorporated by reference herein in its entirety.

BACKGROUND OF THE INVENTION

1. Field of the Invention

The invention relates to a lancet device having a combined cocking and triggering system. The system may be structured and arranged to cock and automatically trigger the lancet device when activated by a user. The invention also relates to a lancet device which is easier to use and/or more economical and which is more efficient to make. The invention also relates to a lancet device preferably having an adjusting capability, and a method of using a lancet device. In particular, the invention relates to a lancet device which can be used with one hand and which can be part of a meter device. The lancet device can also have adjustable depth penetration. The present device also specifically allows the user to cock and trigger the lancet device using only one hand, i.e., one-handed operation.

2. Discussion of Background Information

Lancet devices are used to penetrate and puncture the skin in order to allow the taking of a blood sample for testing. In particular, lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. Nos. 5,797,942 and 5,908,434. These patents are incorporated by reference herein in their entirety and are therefore only briefly discussed herein. Similarly, U.S. Pat. No. 6,156,051 discloses a lancet device which utilizes a lancet firing mechanism, a depth adjustment mechanism, and a trigger setting mechanism. This patent is incorporated by reference herein in its entirety.

What is needed is a system that is structured and arranged to cock and trigger (e.g., automatically trigger and/or substantially simultaneously trigger during cocking) the lancet device when activated by a user. What is also needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices. It is further also desirable to allow the user to cock and trigger the lancet device using only one hand, i.e., one-handed operation. Still further, because many conventional lancet devices can possibly be cocked and/or triggered by accidentally, e.g., such as by dropping the lancet device on the floor, a need exists for a lancet device which cannot be triggered accidentally.

Thus, while advances have been made, there is a continuing need for a lancet device which provides for convenient, reliable and easy adjustment of penetration depth.

SUMMARY OF THE INVENTION

According to one aspect of the invention there is provided a lancet device comprising a skin engaging end that includes a lancet opening through which a lancet needle may extend, a movably mounted holding member configured to receive a lancet, and a combined triggering and cocking system structured and arranged to move the holding member to a retracted position during a cocking phase and to cause the holding member to move to an extended position during a triggering phase.

The combined triggering and cocking system can be activated manually and automatically causes the holding member to move to the extended position during the triggering phase. The combined triggering and cocking system may perform the cocking phase before the triggering phase. The combined triggering and cocking system may activate the cocking phase and the triggering phase using linear movement. The combined triggering and cocking system may comprise at least one push-button. The combined triggering and cocking system may comprise at least one push-button mounted to one of two opposite sides of the lancet device. The combined triggering and cocking system may comprise two push-buttons mounted to opposite sides of the lancet device. The combined triggering and cocking system may comprise a push-button biased towards an extended position. The combined triggering and cocking system may comprise at least one push-button biased towards an extended position and movable towards a central axis of the holding member. The combined triggering and cocking system may, during the cocking phase, automatically cause triggering and/or substantially simultaneously cause triggering.

The lancet device may comprise a meter lancet device. The lancet device may comprise a blood glucose monitoring system. The lancet device may comprise a blood glucose meter. The combined triggering and cocking system may be prevented from moving back to an original position after the triggering phase. The combined triggering and cocking system may be prevented from moving back to an original position after the cocking phase. The combined triggering and cocking system may be prevented from moving back to an original position after the cocking and triggering phases. At least one of the lancet device has an adjustable depth of penetration arrangement, the lancet device is a single-use lancet device, and the lancet device is a multiple-use lancet device.

The lancet device may further comprise a front cover movably connected to one end of a body of the lancet device. The lancet device further comprise a front cover removably connected to one end of a body of the lancet device. The lancet device may further comprise a front cover adjustably mounted to one end of a body of the lancet device. The front cover may adjust a depth of penetration of the lancet needle. The front cover may comprise a one-piece plastic or synthetic resin member. The front cover may comprise an arrangement for guiding movement of the lancet. The front cover may comprise an arrangement for biasing the lancet away from the extended position. The front cover may comprise an arrangement limiting movement of the lancet towards the extended position.

The lancet device may further comprise a first spring structured and arranged to cause movement of the holding member towards the extended position and a second spring structured and arranged to cause movement of the holding member away from the extended position. The first spring may be larger in diameter than the second spring. The first spring may be made from a wire having a larger diameter than a wire of the second spring. Each of the first and the second springs may comprise helical compression springs. The second spring may have one end coupled to a portion of a removable front cap. The second spring may be removable with a front cap.

The lancet device may further comprise a first spring structured and arranged to cause movement of the holding member towards the extended position, a second spring structured and arranged to cause movement of the holding member away from the extended position, and a third spring structured and arranged to resist movement of the combined triggering and cocking system. The lancet device may further comprise a first spring structured and arranged to cause movement of the holding member towards the extended position, a second spring structured and arranged to cause movement of the holding member away from the extended position, and a third spring structured and arranged to compress during activation of the combined triggering and cocking system. The lancet device may further comprise a first spring structured and arranged to cause movement of the holding member towards the extended position, a second spring structured and arranged to cause movement of the holding member away from the extended position, and a third spring structured and arranged to increase in potential energy upon manual movement of a push-button activating the combined triggering and cocking system.

The lancet device may further comprise a biasing member structured and arranged to resist manual movement of the combined triggering and cocking system. The lancet device may further comprise a biasing member structured and arranged to increase in potential energy upon manual movement of a push-button that activates the combined triggering and cocking system. The lancet device may be structured and arranged to allow for replacement of the lancet and for multiple use. The lancet may be removably connected to the front end of the holding member.

The combined triggering and cocking system may be arranged on a removable front cap. The combined triggering and cocking system may be arranged on a movably mounted front cap. The combined triggering and cocking system may be arranged on a front cap having the skin engaging end. The holding member may comprise a generally cylindrical cross-section. The holding member may comprise a generally polygonal cross-section. The lancet device may further comprise a fixed stop surface that is contacted by a movable stop surface of the holding member when the holding member moves to an extended position. A front end of the holding member may comprise an opening that is configured to removably receive the lancet. The lancet device may further comprise indicia arranged on at least one of an intermediate member and a body of the lancet device. The indicia may be arranged on an outer circumferential surface. The lancet device may further comprise a front cover that rotates about an axis that runs through the lancet opening and the holding member. The lancet device may comprise a two-piece body. The lancet device may comprise an ergonomic shape.

The invention also provides for a method of puncturing a surface of skin using the lancet device of the type described above, wherein the method comprises disposing the skin engaging end against a user's skin and manually activating the combined triggering and cocking system. The manually activating may cause the combined triggering and cocking system to automatically cause triggering and/or substantially simultaneously cause triggering.

The invention also provides for a method of puncturing a surface of skin using the lancet device of the type described above, wherein the method comprises adjusting a set depth of penetration by rotating the intermediate member to a desired set position, disposing the skin engaging end against a user's skin, and manually activating the combined triggering and cocking system.

The invention also provides for a lancet device cap comprising a skin engaging end that includes a lancet opening through which a lancet needle may extend, an arrangement for connecting or mounting the lancet device cap to at least one of a lancet device body and a meter, and a manually activated combined triggering and cocking system structured and arranged to move a holding member and/or the lancet to a retracted position during a cocking phase and to cause the holding member and/or the lancet to move to an extended position during a triggering phase.

The invention also provides for a blood glucose monitoring system comprising a meter, a skin engaging end that includes a lancet opening through which a lancet needle may extend, a movably mounted holding member configured to receive a lancet, and a manually activated combined triggering and cocking system structured and arranged to move the holding member and/or the lancet to a retracted position during a cocking phase and to cause the holding member and/or the lancet to move to an extended position during a triggering phase.

The invention also provides for a monitoring system comprising a meter, an arrangement for adjusting depth of penetration, a skin engaging end that includes a lancet opening through which a lancet needle may extend, a combined triggering and cocking system structured and arranged to move the lancet to a retracted position during a cocking phase and to cause the lancet to move to an extended position during a triggering phase.

The arrangement for adjusting depth of penetration may comprise a front cap having the skin engaging end that includes a lancet opening through which a lancet needle may extend. The front cap may comprise the combined triggering and cocking system. The lancet device of the invention is also, by way of non-limiting example, configured to prevent it from being triggered accidentally.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 41 shows another front side view of the push-button cocking and triggering member used in the embodiment shown in FIGS. 37-40;

FIG. 42 shows a top view of the push-button cocking and triggering member shown in FIG. 41;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 5:
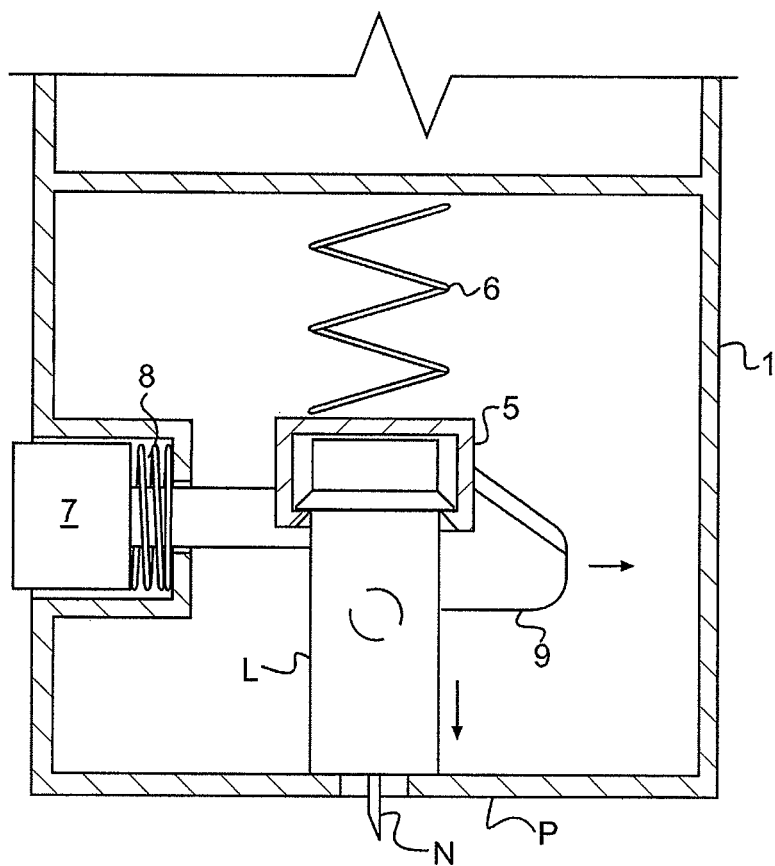
FIG. 5 shows a partial side cross-section view of the first embodiment shown in FIG. 1. The push-button cocking and triggering system is shown in the triggering phase whereby the lancet holding member and/or lancet is moved to an extended or puncturing position.
Figure 6:
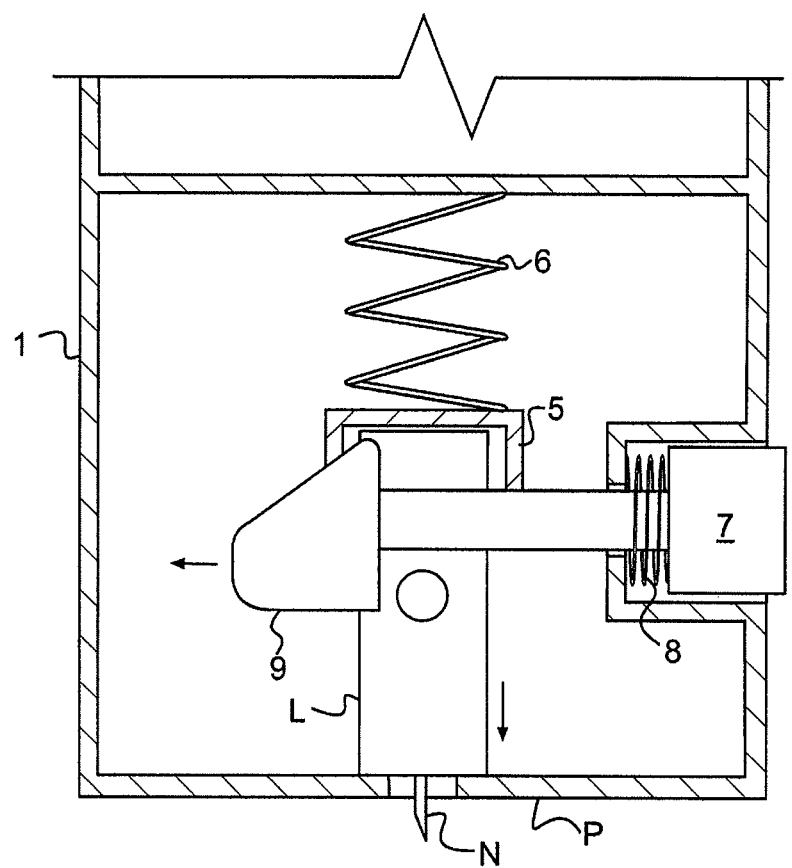
FIG. 6 shows an opposite or rear side view of FIG. 5.
Figure 7:
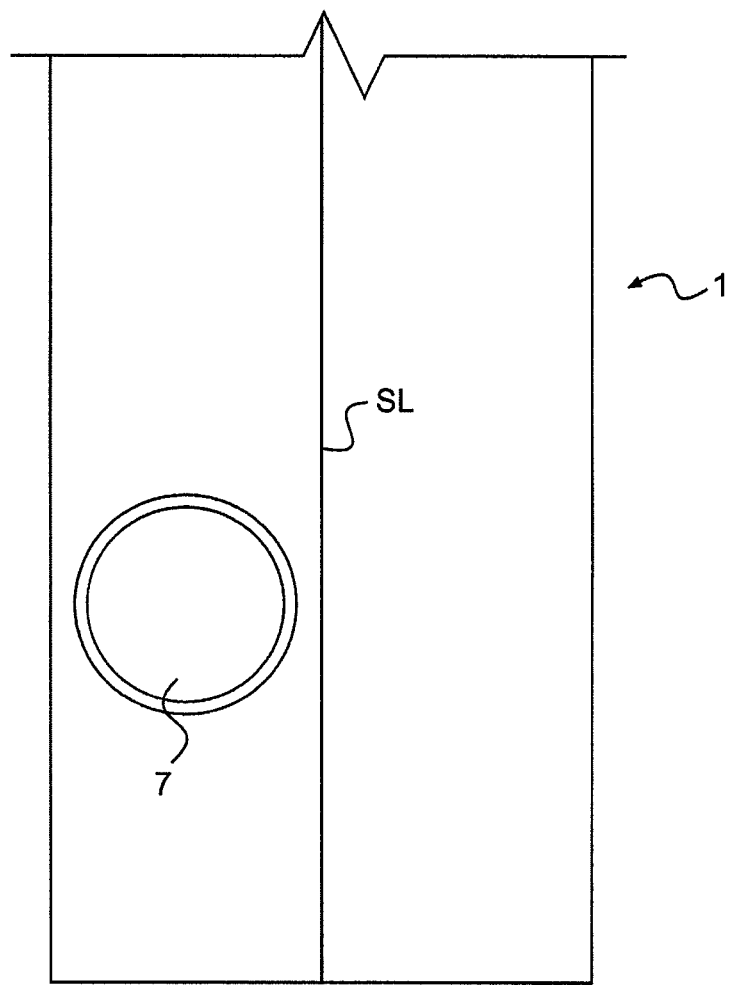
FIG. 7 shows a left side view of the embodiment shown in FIG. 1 and illustrates the position of the push-button.

FIGS. 1-7 show a first non-limiting embodiment of a lancet device or lancet device portion of a meter, e.g., a blood glucose monitoring meter. The device has a meter portion MP which can be of any type whether conventional or otherwise and which details are generally known and therefore not shown. The device also has a lancet device or lancet device portion LDP. The lancet device portion LDP has a body 1 which can be made as a one-piece member with the body of the meter portion MP or alternatively as a two-piece body made up of two body parts which are connected together, e.g., via a seam line SL, as shown in FIG. 7. Such body parts can, of course, be connected, e.g., using adhesives and/or fasteners and/or welding and/or snap-together holding mechanisms (not shown) to each other when the lancet device LDP is initially assembled. A holding member 5 is movably disposed within the body 1. Although not shown, a front cover (similar to that shown in FIG. 8) is removably connected or attached to an end of the body 1. By removing the front cover, a user can gain access to the lancet L. The lancet L can thus be removed and replaced with a new lancet L, as needed, once the front cover is removed. As in known lancet devices, the lancet device LDP defines a plane P which is configured to contact (i.e., be positioned against) a user's skin. Although not shown, the instant embodiment may also utilize an inwardly curved and/or an outwardly curved surface plane P beyond which the lancet need can extend. The lancet holder 5 has a front portion 4 that can be accessed by a user upon removal of the front cover in order to all for replacement of the lancet L. The holding member 5 slides within the body 1 and more specifically slides within one or more openings (not show). As will be described in more detail later on, movement of the holding member 5 rearwardly, causes the holding member 5 to retract until it reaches a spring loaded position shown in FIGS. 3 and 4. The lancet L includes a needle N and can be removed and replaced with a new lancet, as is the case in many lancet devices. To ensure that lancet L is securely (yet removably) retained within the lancet device LDP, the front portion 4 of the holding member 5 includes a lancet holding opening 5*a* which receives the lancet L therein.

As can be seen in FIGS. 1-6, the holding member 5 preferably has a spring 6 mounted thereto. In this regard, the spring 6, which can be made of spring steel, functions to cause the holding member 5 to move towards the extended or puncturing position (see FIGS. 5 and 6). By way of one non-limiting example, the spring 6 may have a diameter of between approximately 3 mm and approximately 15 mm, a freelength of between approximately 5 mm and approximately 40 mm, and a wire size of between approximately 0.5 mm and 2 mm. This first spring 6 causes (and/or biases) the holding member 5 to move towards an extended position once a cocking/trigger mechanism 9 is activated (causing the movement indicated by arrows in FIGS. 5 and 6). The cocking/trigger mechanism 9 is arranged at an opposite end of a push-button 7 and has a cylindrical portion that is surrounded by a spring 8. The cocking/trigger mechanism 9 has a tapered surface 9*a* is configured to slidably engage with a protruding projection PP arranged on the lancet L. In the position shown in FIGS. 1 and 2, the tapered surface 9*a* has not yet slidably engaged with the protruding projection PP arranged on the lancet L. Furthermore, the spring 8 is in an extended position which biases the push-button 7 and, of course, the cocking/trigger mechanism 9 which is fixed thereto, towards an original pre-cocking and pre-triggering position.

Figure 1:
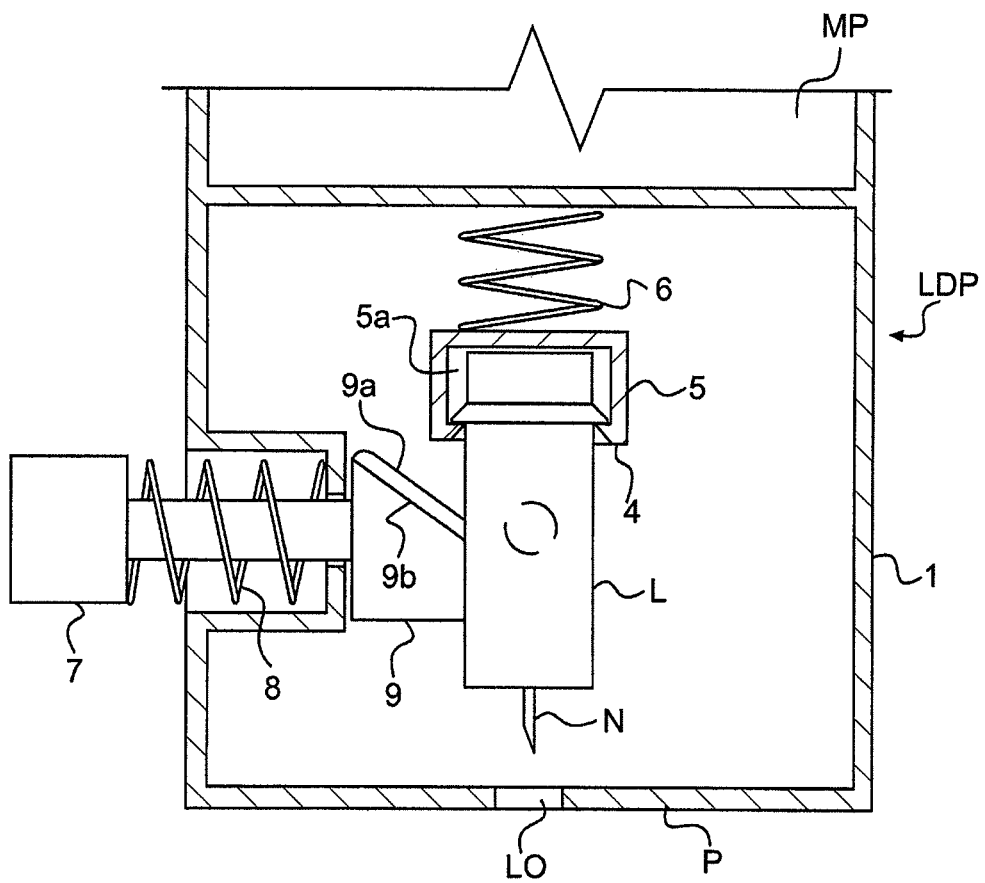
FIG. 1 shows a partial front side cross-section view of a first embodiment of the lancet device or lancet device portion of a meter. This embodiment utilizes a push-button trigger setting and/or cocking system and triggering system which is shown in an initial non-cocking and non-triggering position. The lancet is not shown in cross-section and the arrangement for guiding the lancet holding member is not shown.
Figure 2:
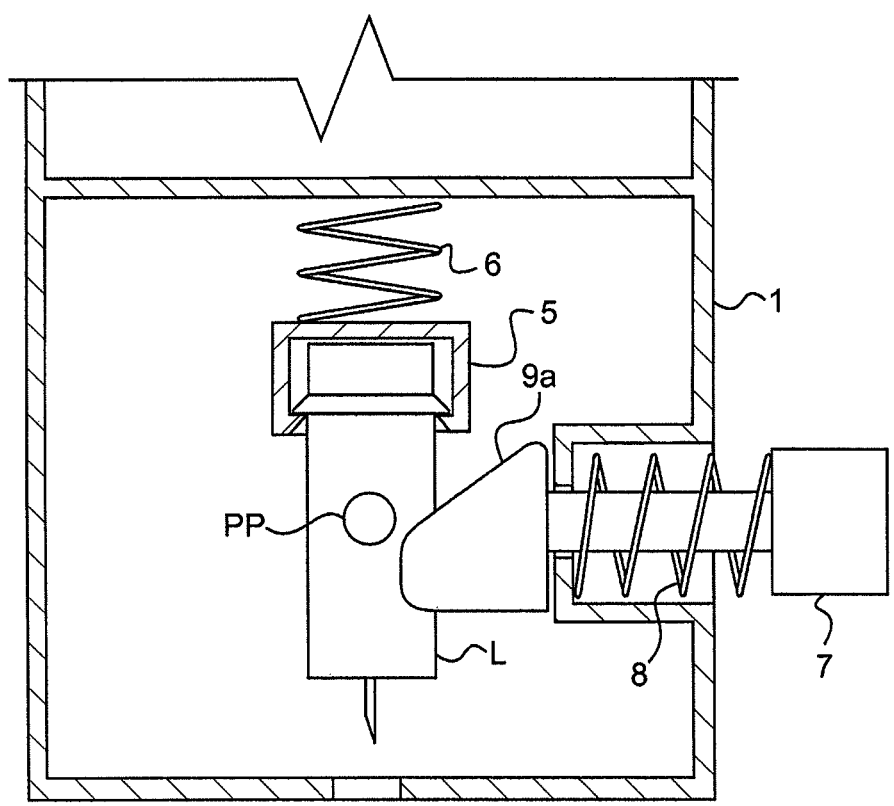
FIG. 2 shows an opposite or rear side view of FIG. 1.
Figure 3:
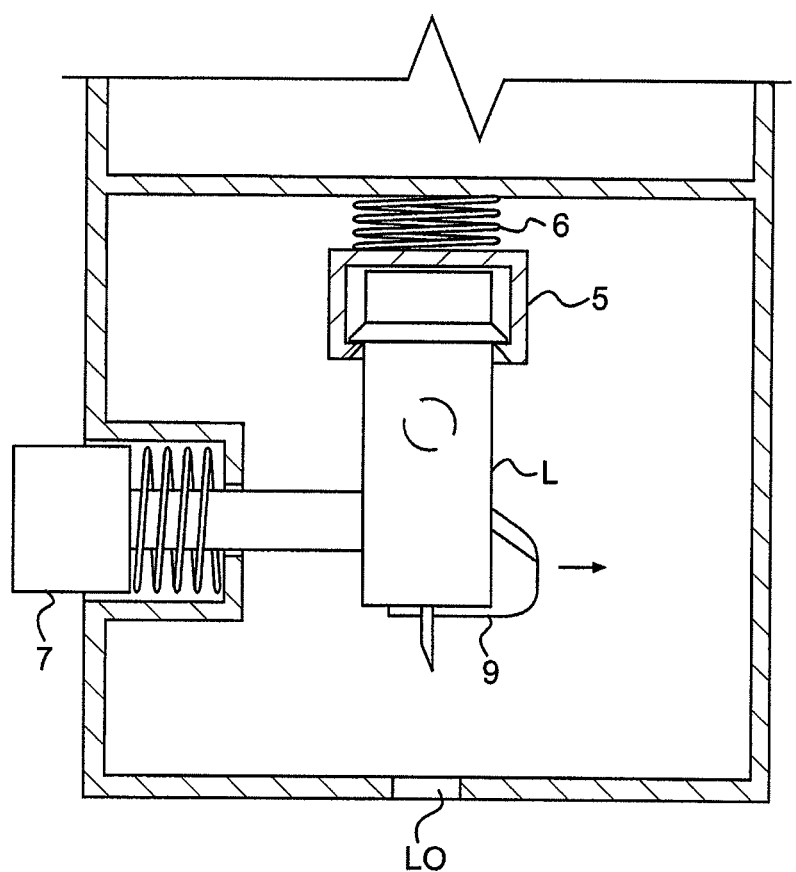
FIG. 3 shows a partial side cross-section view of the first embodiment shown in FIG. 1. The push-button cocking and triggering system is shown in the cocking phase whereby the lancet holding member and/or lancet is moved to a retracted position.
Figure 4:
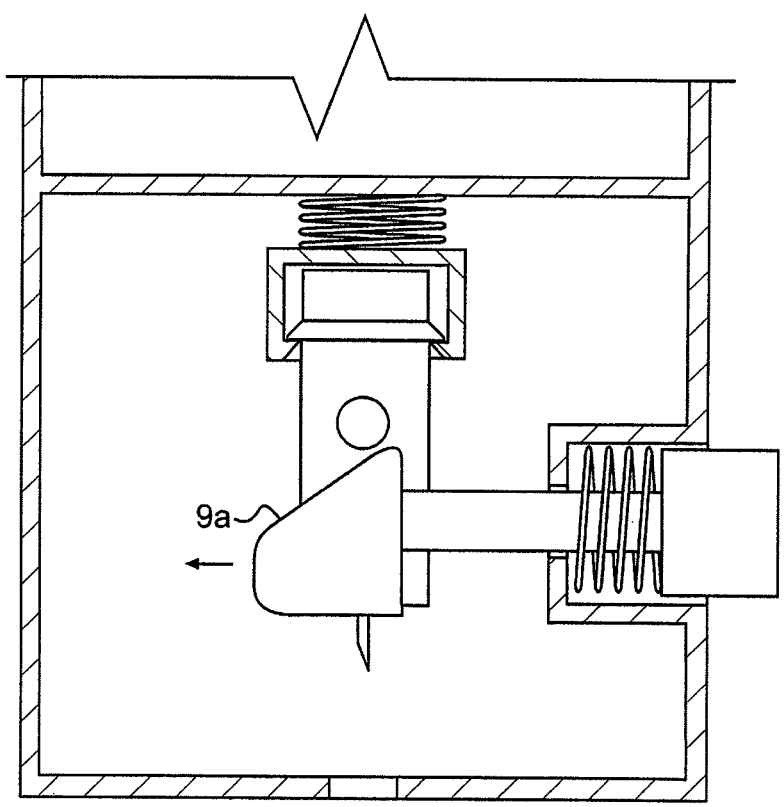
FIG. 4 shows an opposite or rear side view of FIG. 3.

In operation, when force is applied to the finger engaging push-button 7, the tapered surface 9*a* moves into contact with projecting portion PP (see FIGS. 3 and 4). This engagement causes the lancet L and the holding member 5 to progressively move away from the lancet opening LO which in turn compresses the spring 6. Eventually, this engagement reaches a maximum point (maximum compression of the spring 6 and maximum movement of the lancet L and the holding member 5 away from the lancet opening LO). At that point, any further movement of the cocking/trigger mechanism 9 causes or allows the spring 6 to release its energy and move the lancet L and the holding member 5 towards the lancet opening LO (see FIGS. 5 and 6). Eventually, this movement of member 9 reaches a maximum point (maximum compression of the spring 8 and maximum inward movement of the push-button 7).

Figure 28:
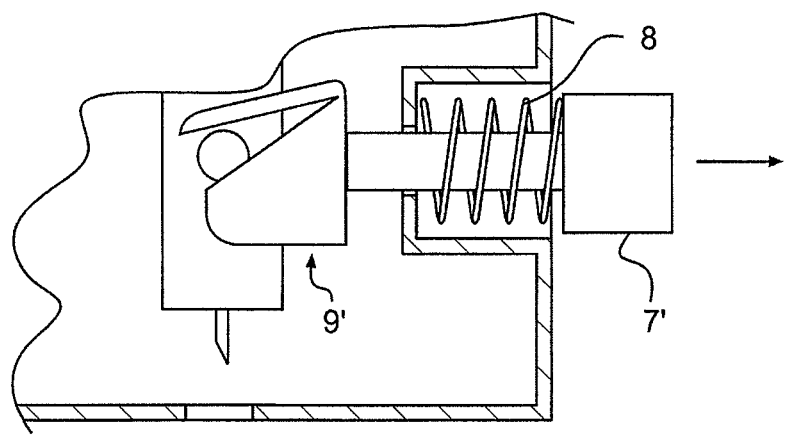
FIG. 28 shows a partial cross-section view of an embodiment similar to that shown in FIG. 2 but utilizing the member shown in FIGS. 24-27. The position shown is before the push-button cocking and triggering member moves back to the extended position shown in FIG. 2, and illustrates how a deflecting portion of the push-button cocking and triggering member is caused to deflect outwardly by the projecting pin of the lancet as the push-button cocking and triggering member moves back to the extended position shown in FIG. 2.
Figure 29:
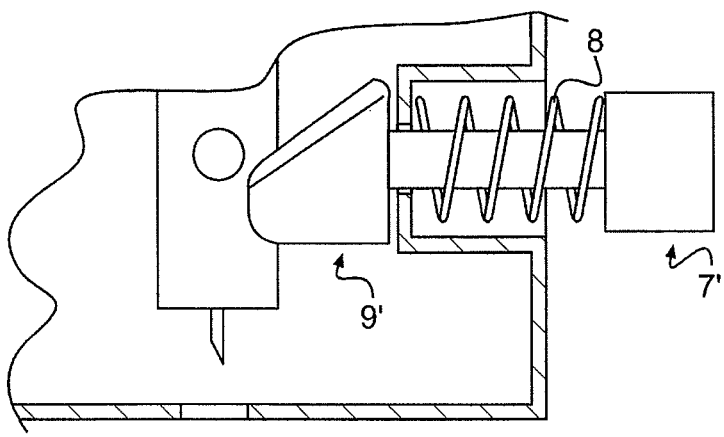
FIG. 29 shows the view of FIG. 28 after the push-button cocking and triggering member moves back to the extended position. The lancet device is now ready to be cocked and triggered again.
Figure 30:
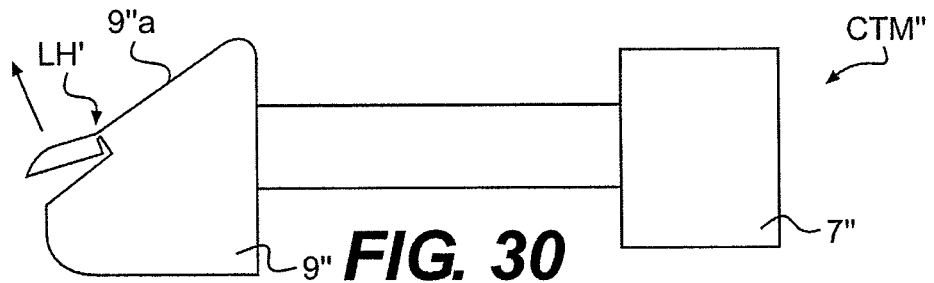
FIG. 30 shows a rear side view of another embodiment of the push-button cocking and triggering member which can be used in one or more of the embodiments shown in FIGS. 1-19.
Figure 31:
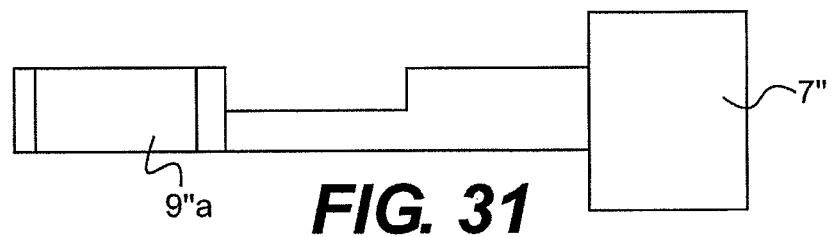
FIG. 31 shows a top view of FIG. 30.
Figure 32:
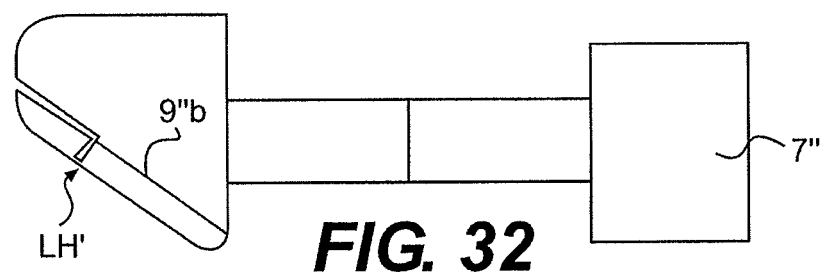
FIG. 32 shows an opposite side view of FIG. 30.
Figure 33:
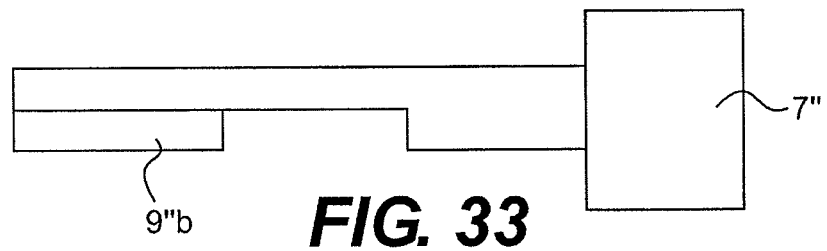
FIG. 33 shows an opposite side view of FIG. 31.

As is shown in FIGS. 5 and 6, the maximum movement of the lancet L is characterized by the lancet needle N extending through the lancet opening LO and past the plane P to thereby cause a puncturing of a user's skin. The amount that the needle N projects past the plane P is determined, by way of non-limiting example, by contact between the proximal end of the lancet L and the inside surface of the body 1 in the area of the lancet opening LO and just behind the plane P. Of course, this maximum movement causing a puncturing of a user's skin as shown in FIGS. 5 and 6 occurs for only a fraction of a second. Then, the spring 6 (or another spring not shown) will cause the lancet L and the holding member 5 to move back to the intermediate position shown in FIGS. 1 and 2. At this point, the user can remove his or her finger from the push-button 7. Then, the spring 8 will automatically expand and cause the member 9 to move in a direction opposite to the direction of cocking and triggering. This movement will cause underside surface 9*b* of member 9 to engage the projecting portion PP by a small amount which, in turn, will cause the lancet L and holding member 5 to move towards the lancet opening LO. However, this amount is small and not sufficient to cause the needle N to move through the lancet opening LO. On the other hand, this movement of the lancet L in response to movement of the member 9 back to the original position shown in FIGS. 1 and 2, can be prevented by configuring the member 9 with a deflecting portion shown in FIGS. 24-27 and/or 30-33. FIGS. 28 and 29 illustrate one non-limiting way in which this would occur using the cocking and triggering member shown in FIGS. 24-27.

Figure 8:
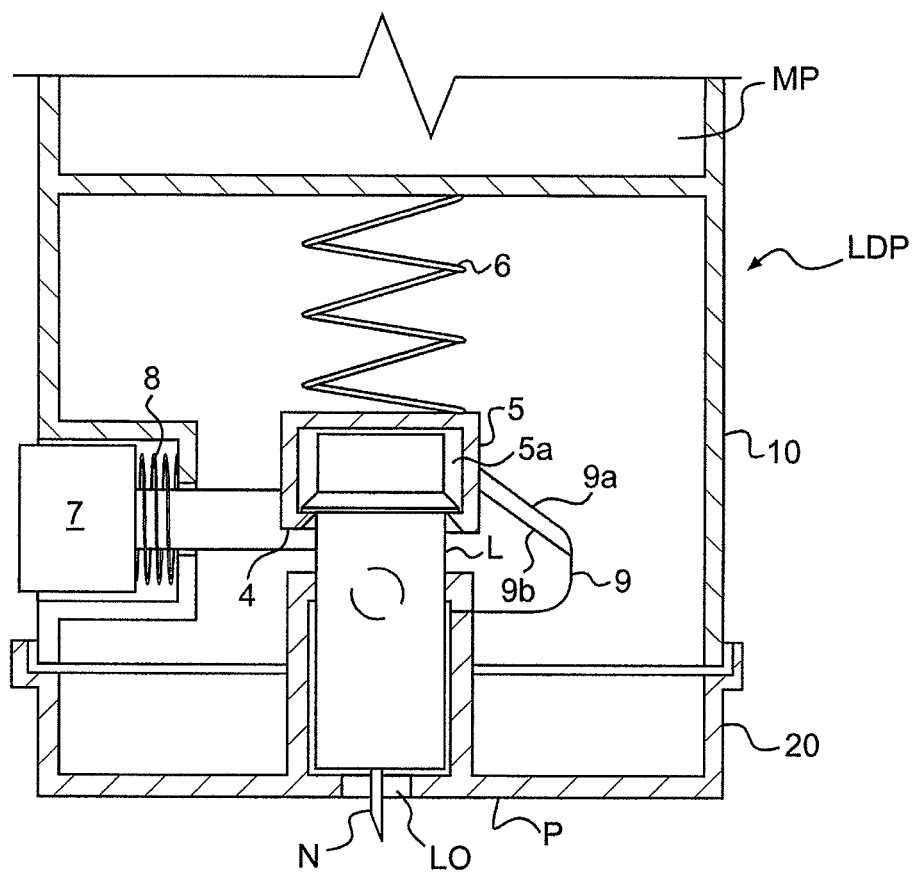
FIG. 8 shows a partial front side cross-section view of a second embodiment of the lancet device or lancet device portion of a meter. This embodiment utilizes a removable front cap and a push-button trigger setting and/or cocking system and triggering system which is shown in post-cocking and post-triggering position. The lancet is not shown in cross-section and the arrangement for guiding the lancet holding member is not shown.
Figure 9:
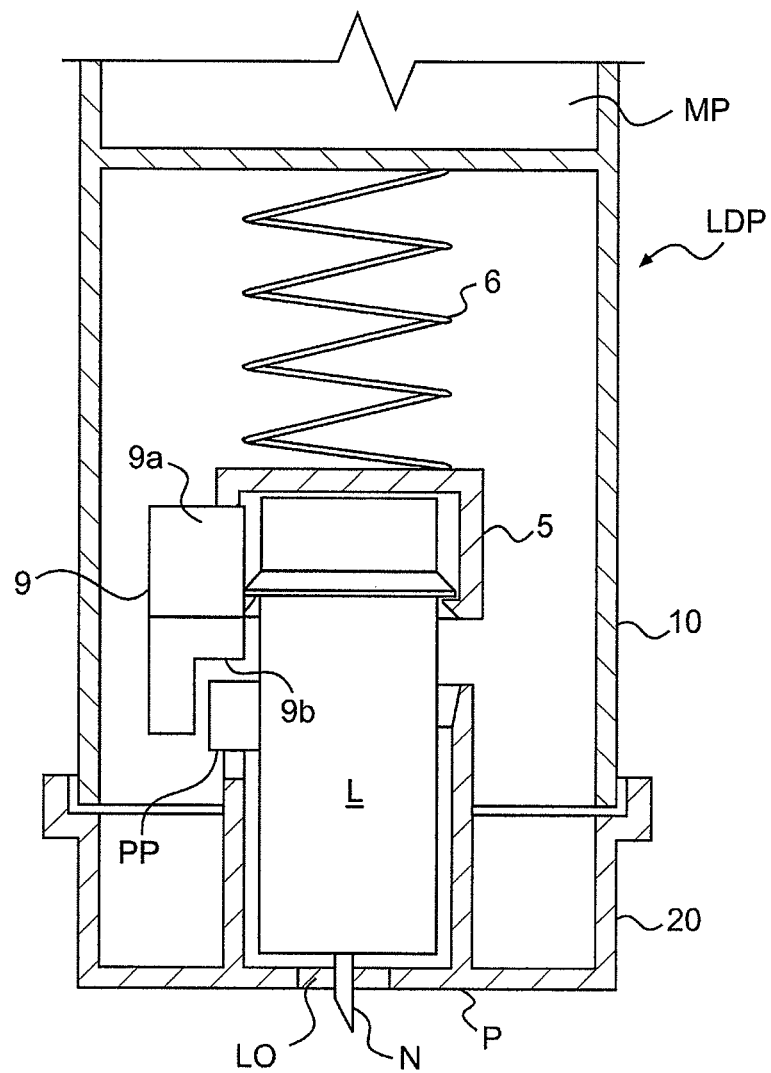
FIG. 9 shows a right side cross-section view of the embodiment shown in FIG. 8.
Figure 10:
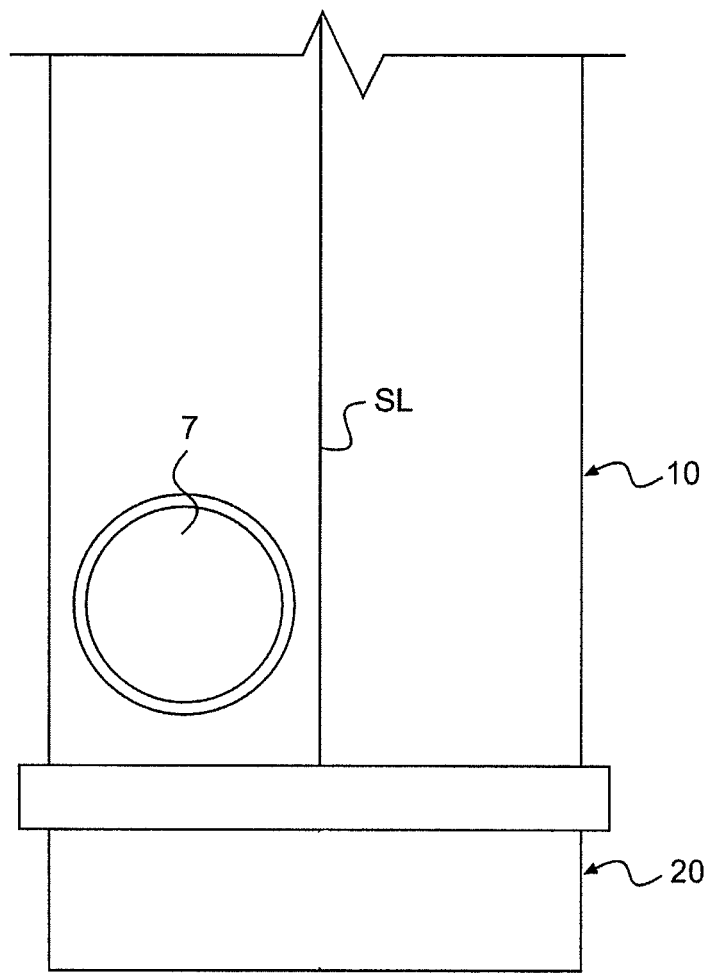
FIG. 10 shows a left side view of the embodiment shown in FIG. 8.

FIGS. 8-12 show a second non-limiting embodiment of a lancet device or lancet device portion of a meter, e.g., a blood glucose monitoring meter. The device also has a meter portion MP which can be of any type whether conventional or otherwise and which details are generally known and therefore not shown. The device also has a lancet device or lancet device portion LDP. The lancet device portion LDP has a body 10 which can be made as a one-piece member with the body of the meter portion MP or alternatively as a two-piece body made up of two body parts which are connected together, e.g., via a seam line SL, as shown in FIG. 10. Such body parts can, of course, be connected, e.g., using adhesives and/or fasteners and/or welding and/or snap-together holding mechanisms (not shown) to each other when the lancet device LDP is initially assembled. A holding member 5 is movably disposed within the body 10. A front cover 20 is removably connected or attached to an end of the body 10. By removing the front cover 20, a user can gain access to the lancet L. The lancet L can thus be removed and replaced with a new lancet L, as needed, once the front cover 20 is removed. As in known lancet devices, the lancet device LDP defines a plane P which is configured to contact (i.e., be positioned against) a user's skin. Although not shown, the instant embodiment may also utilize an inwardly curved and/or an outwardly curved surface plane P beyond which the lancet need can extend. The lancet holder 5 has a front portion 4 that can be accessed by a user upon removal of the front cover in order to all for replacement of the lancet L. The holding member 5 slides within the body 1 and more specifically slides within one or more openings (not show). As will be described in more detail later on, movement of the holding member 5 rearwardly, causes the holding member 5 to retract until it reaches a spring loaded position (similar to that shown in FIGS. 3 and 4). The lancet L includes a needle N and can be removed and replaced with a new lancet, as is the case in many lancet devices. To ensure that lancet L is securely (yet removably) retained within the lancet device LDP, the front portion 4 of the holding member 5 includes a lancet holding opening 5*a* which receives the lancet L therein.

As can be seen in FIGS. 8 and 9, the holding member 5 preferably has a spring 6 mounted thereto. In this regard, the spring 6, which can be made of spring steel, functions to cause the holding member 5 to move towards the extended or puncturing position (see FIGS. 8 and 9). By way of one non-limiting example, the spring 6 may have a diameter of between approximately 3 mm and approximately 15 mm, a freelength of between approximately 5 mm and approximately 40 mm, and a wire size of between approximately 0.5 mm and 2 mm. This first spring 6 causes (and/or biases) the holding member 5 to move towards an extended position once a cocking/trigger mechanism 9 is activated (causing the same movement as indicated by arrows in FIGS. 5 and 6). The cocking/trigger mechanism 9 is arranged at an opposite end of a push-button 7 and has a cylindrical portion that is surrounded by a second spring 8. As in the previous embodiment, the cocking/trigger mechanism 9 has a tapered surface 9*a* is configured to slidably engage with a protruding projection PP arranged on the lancet L. In the position shown in FIGS. 8 and 9, the tapered surface 9a has previously engaged with the protruding projection PP arranged on the lancet L. Furthermore, the spring 8 has reached a compressed position but continues to bias the push-button 7 and, of course, the cocking/trigger mechanism 9 which is fixed thereto, towards an original pre-cocking and pre-triggering position (similar to FIGS. 1 and 2).

In operation, when force is applied to the finger engaging push-button 7, the tapered surface 9a moves into contact with projecting portion PP (similar to FIGS. 3 and 4). This engagement causes the lancet L and the holding member 5 to progressively move away from the lancet opening LO which in turn compresses the spring 6. Eventually, this engagement reaches a maximum point (maximum compression of the spring 6 and maximum movement of the lancet L and the holding member 5 away from the lancet opening LO). At that point, any further movement of the cocking/trigger mechanism 9 causes or allows the spring 6 to release its energy and move the lancet L and the holding member 5 towards the lancet opening LO (see FIGS. 8 and 9). Eventually, this movement of member 9 reaches a maximum point (maximum compression of the spring 8 and maximum inward movement of the push-button 7).

As is shown in FIGS. 8 and 9, the maximum movement of the lancet L is characterized by the lancet needle N extending through the lancet opening LO and past the plane P to thereby cause a puncturing of a user's skin. The amount that the needle N projects past the plane P is determined, by way of non-limiting example, by contact between the proximal end of the lancet L and the inside surface of the front cap 20 in the area of the lancet opening LO and just behind the plane P. Of course, this maximum movement causing a puncturing of a user's skin as shown in FIGS. 8 and 9 occurs for only a fraction of a second. Then, the spring 6 (or another spring not shown) will cause the lancet L and the holding member 5 to move back to the intermediate position (similar to that shown in FIGS. 1 and 2). At this point, the user can remove his or her finger from the push-button 7. Then, the spring 8 will automatically expand and cause the member 9 to move in a direction opposite to the direction of cocking and triggering. This movement will cause underside surface 9b of member 9 to engage the projecting portion PP by a small amount which, in turn, will cause the lancet L and holding member 5 to move towards the lancet opening LO. This amount of movement is small, however, and not sufficient to cause the needle N to move through the lancet opening LO. On the other hand, this movement of the lancet L in response to movement of the member 9 back to the original position (see e.g., FIGS. 1 and 2), can be prevented by configuring the member 9 with a deflecting portion shown in FIGS. 24-27 and/or 30-33. FIGS. 28 and 29 illustrate one non-limiting way in which this would occur using the cocking and triggering member shown in FIGS. 24-27.

Figure 11:
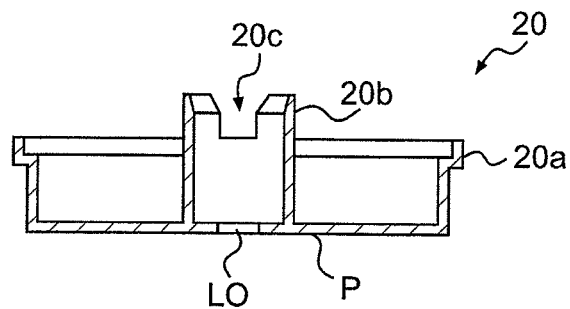
FIG. 11 shows a front side cross-section view of the front cap used in the embodiment shown in FIG. 8.
Figure 12:
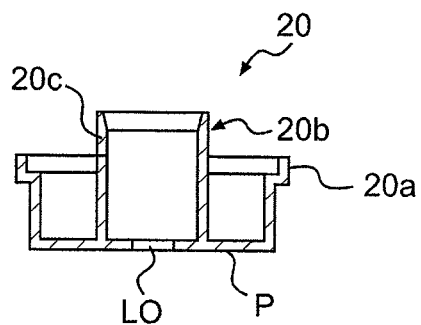
FIG. 12 shows a left side cross-section view of the front cap used in the embodiment shown in FIG. 8.

As can be seen in FIGS. 11 and 12, the front cap 20 has a generally rectangular configuration and utilizes a connecting flange area 20a which is configured to releasably engage with a proximal end of the body 10. This can occur by way of locking projections, or any other way, whether conventional or otherwise, of releasably connecting the front cap 20 to the body 10. Of course, if the front cap 20 is round or circular, internal threads can be utilized on the inside surface of flange area 20a so that the front cap 20 can be threadably connected to the proximal end of the body 10. The front cap 20 also has a guiding sleeve portion 20b which is configured to guide (e.g., using sliding engagement) the linear movement of the lancet L as it moves towards the lancet opening LO. The front cap 20 additionally has a guiding recess 20c which is configured to guide (e.g., using sliding engagement) the linear movement of the projecting portion PP as the lancet L moves towards the lancet opening LO and prevents the lancet L from rotating more than a predetermined amount. This, in turn, ensures that there is proper engagement between the projecting portion PP and surface 9a. The amount that the needle N projects past the plane P can also be determined, by way of non-limiting example, by contact between the projecting portion PP and the bottom surface of the recess 20c instead of (or in addition to) contact between proximal end of the lancet L and the inside surface of the body 10 in the area of the lancet opening LO and just behind the plane P. The front cap 20 can preferably be made as a one-piece member or alternatively as a two-piece member made up of two parts which are connected together.

Figure 13:
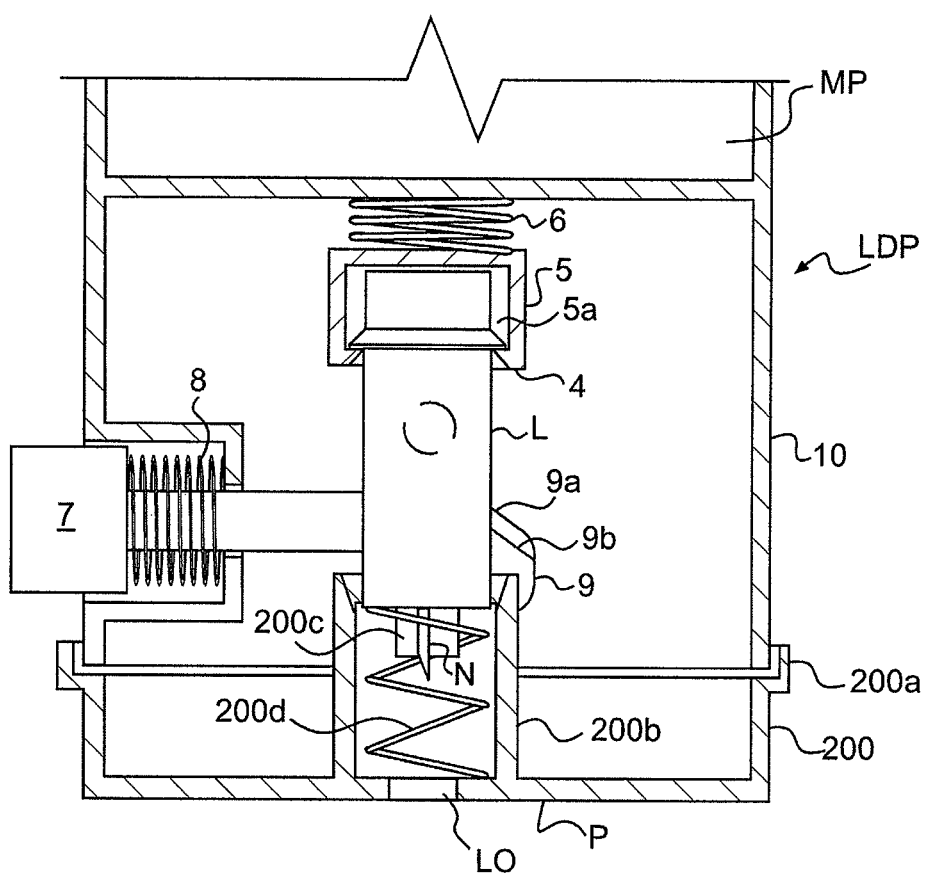
FIG. 13 shows a partial front side cross-section view of a third embodiment of the lancet device or lancet device portion of a meter. This embodiment utilizes a removable front cap and a push-button trigger setting and/or cocking system and triggering system which is shown in post-cocking and post-triggering position. The front cap utilizes a spring to bias the lancet towards an intermediate position after the lancet moves to the extended position. The lancet is not shown in cross-section and the arrangement for guiding the lancet holding member is not shown.
Figure 14:
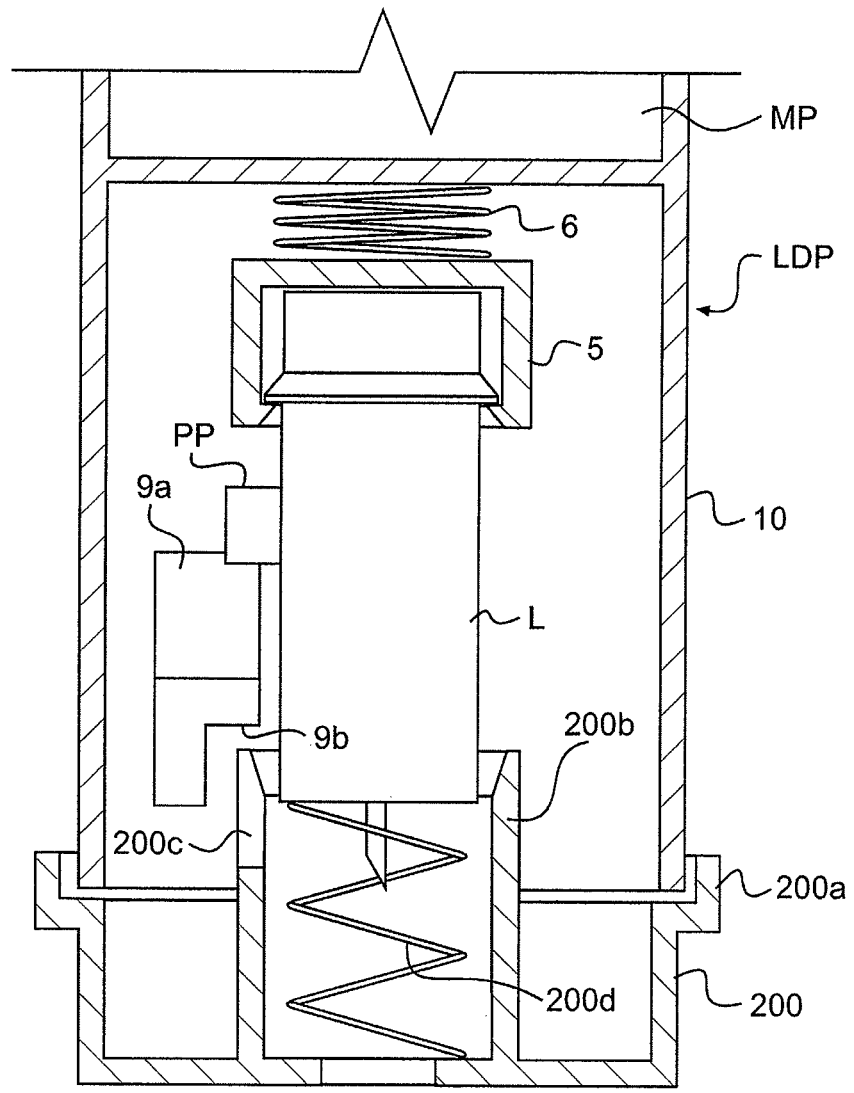
FIG. 14 shows a right side cross-section view of the embodiment shown in FIG. 13.

FIGS. 13 and 14 show a third non-limiting embodiment of a lancet device or lancet device portion of a meter, e.g., a blood glucose monitoring meter. The device also has a meter portion MP which can be of any type whether conventional or otherwise and which details are generally known and therefore not shown. The device also has a lancet device or lancet device portion LDP. The lancet device portion LDP has a body 10 which can be made as a one-piece member with the body of the meter portion MP or alternatively as a two-piece body made up of two body parts which are connected together (e.g., via a seam line SL as shown in FIG. 10). Such body parts can, of course, be connected, e.g., using adhesives and/or fasteners and/or welding and/or snap-together holding mechanisms (not shown) to each other when the lancet device LDP is initially assembled. A holding member 5 is movably disposed within the body 10. A front cover 200 is removably connected or attached to an end of the body 10. By removing the front cover 200, a user can gain access to the lancet L. The lancet L can thus be removed and replaced with a new lancet L, as needed, once the front cover 200 is removed. As in known lancet devices, the lancet device LDP defines a plane P which is configured to contact (i.e., be positioned against) a user's skin. Although not shown, the instant embodiment may also utilize an inwardly curved and/or an outwardly curved surface plane P beyond which the lancet need can extend. The lancet holder 5 has a front portion 4 that can be accessed by a user upon removal of the front cover in order to all for replacement of the lancet L. The holding member 5 slides within the body 1 and more specifically slides within one or more openings (not show). As will be described in more detail later on, movement of the holding member 5 rearwardly, causes the holding member 5 to retract until it reaches a spring loaded position shown in FIGS. 13 and 14. The lancet L includes a needle N and can be removed and replaced with a new lancet, as is the case in many lancet devices. To ensure that lancet L is securely (yet removably) retained within the lancet device LDP, the front portion 4 of the holding member 5 includes a lancet holding opening 5a which receives the lancet L therein.

As can be seen in FIGS. 13 and 14, the holding member 5 preferably has a spring 6 mounted thereto. In this regard, the spring 6, which can be made of spring steel, functions to cause the holding member 5 to move towards the extended or puncturing position (see e.g., FIGS. 8 and 9). By way of one non-limiting example, the spring 6 may have a diameter of between approximately 3 mm and approximately 15 mm, a freelength of between approximately 5 mm and approximately 40 mm, and a wire size of between approximately 0.5 mm and 2 mm. This first spring 6 causes (and/or biases) the holding member 5 to move towards an extended position once a cocking/trigger mechanism 9 is activated (causing the same movement as indicated by arrows in FIGS. 5 and 6). The cocking/trigger mechanism 9 is arranged at an opposite end of a push-button 7 and has a cylindrical portion that is surrounded by a second spring 8. As in the previous embodiment, the cocking/trigger mechanism 9 has a tapered surface 9a is configured to slidably engage with a protruding projection PP arranged on the lancet L. In the position shown in FIGS. 13 and 14, the tapered surface 9a is engaging with the protruding projection PP arranged on the lancet L. Furthermore, the spring 8 has reached an intermediate compressed position but continues to bias the push-button 7 and, of course, the cocking/trigger mechanism 9 which is fixed thereto, towards an original pre-cocking and pre-triggering position (similar to FIGS. 1 and 2).

In operation, when force is applied to the finger engaging push-button 7, the tapered surface 9a moves into contact with projecting portion PP (FIGS. 13 and 14). This engagement causes the lancet L and the holding member 5 to progressively move away from the lancet opening LO which in turn compresses the spring 6. Eventually, this engagement reaches a maximum point (maximum compression of the spring 6 and maximum movement of the lancet L and the holding member 5 away from the lancet opening LO). FIGS. 13 and 14 show the lancet L at almost the maximum point of retraction. At that point, any further movement of the cocking/trigger mechanism 9 causes or allows the spring 6 to release its energy and move the lancet L and the holding member 5 towards the lancet opening LO (in the same way as shown in FIGS. 8 and 9). Eventually, this movement of member 9 reaches a maximum point (maximum compression of the spring 8 and maximum inward movement of the push-button 7).

The maximum movement of the lancet L is characterized by the lancet needle N extending through the lancet opening LO and past the plane P to thereby cause a puncturing of a user's skin (see e.g., FIGS. 8 and 9). The amount that the needle N projects past the plane P is determined, by way of non-limiting example, by contact between the proximal end of the lancet L and the inside surface of the front cap 200 (and more specifically full compression of the spring 200d between these surfaces) in the area of the lancet opening LO and just behind the plane P. Of course, this maximum movement causing a puncturing of a user's skin (as exemplified by FIGS. 8 and 9) occurs for only a fraction of a second. Then, the spring 6 aided by a third spring 200d will cause the lancet L and the holding member 5 to move back to the intermediate position (similar to that shown in FIGS. 1 and 2). At this point, the user can remove his or her finger from the push-button 7. Then, the spring 8 will automatically expand and cause the member 9 to move in a direction opposite to the direction of cocking and triggering. This movement will cause underside surface 9b of member 9 to engage the projecting portion PP by a small amount which, in turn, will cause the lancet L and holding member 5 to move towards the lancet opening LO. This amount of movement is small, however, and not sufficient to cause the needle N to move through the lancet opening LO. On the other hand, this movement of the lancet L in response to movement of the member 9 back to the original position (see e.g., FIGS. 1 and 2), can be prevented by configuring the member 9 with a deflecting portion shown in FIGS. 24-27 and/or 30-33. FIGS. 28 and 29 illustrate one non-limiting way in which this would occur using the cocking and triggering member shown in FIGS. 24-27.

As can be seen in FIGS. 13 and 14, the front cap 200 has a generally rectangular configuration and utilizes a connecting flange area 200a which is configured to releasably engage with a proximal end of the body 10. This can occur by way of locking projections, or any other way, whether conventional or otherwise, of releasably connecting the front cap 200 to the body 10. Of course, if the front cap 200 is round or circular, internal threads can be utilized on the inside surface of flange area 200a so that the front cap 200 can be threadably connected to the proximal end of the body 10. The front cap 200 also has a guiding sleeve portion 200b which is configured to guide (e.g., using sliding engagement) the linear movement of the lancet L as it moves towards the lancet opening LO. The front cap 200 additionally has a guiding recess 200c which is configured to guide (e.g., using sliding engagement) the linear movement of the projecting portion PP as the lancet L moves towards the lancet opening LO and prevents the lancet L from rotating more than a predetermined amount. This, in turn, ensures that there is proper engagement between the projecting portion PP and surface 9a. The amount that the needle N projects past the plane P can also be determined, by way of non-limiting example, by contact between the projecting portion PP and the bottom surface of the recess 200c instead of (or in addition to) contact between proximal end of the lancet L and the inside surface of the body 10 in the area of the lancet opening LO and just behind the plane P. The front cap 200 can preferably be made as a one-piece member or alternatively as a two-piece member made up of two parts which are connected together. The third spring 200d causes the lancet L and the holding member 5 to move back to the intermediate position (similar to that shown in FIGS. 1 and 2) and is arranged between the lancet L and the bottom surface of the flange 200b in the area of the lancet opening LO. The third spring 200d also becomes compressed when the lancet L and the holding member 5 move from the retracted position shown in FIGS. 13 and 14 to the fully extended position (see e.g., FIGS. 8 and 9).

Figure 15:
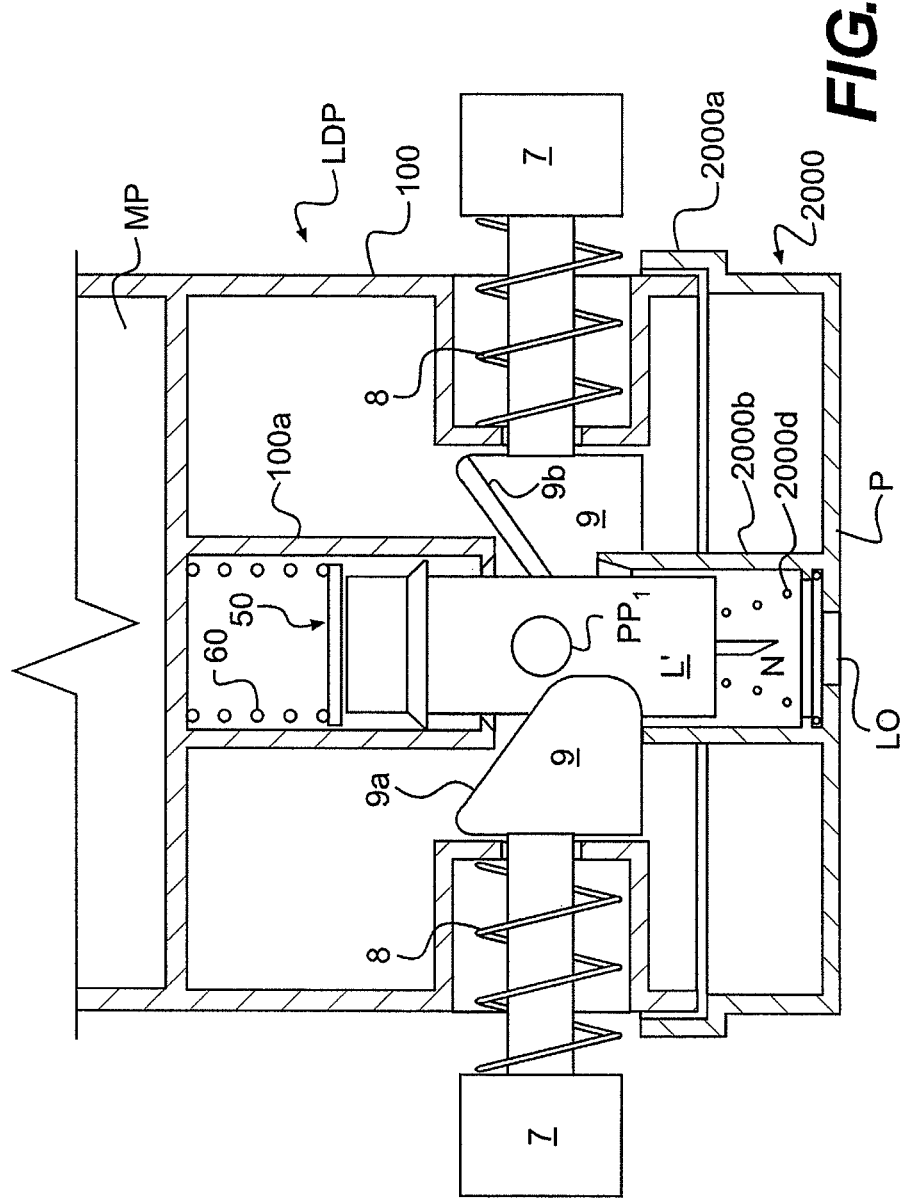
FIG. 15 shows a partial front side cross-section view of a fourth embodiment of the lancet device or lancet device portion of a meter. This embodiment utilizes a removable front cap and a dual push-button trigger setting and/or cocking system and triggering system which is shown in non-cocking and non-triggering position. The front cap utilizes a spring to bias the lancet towards an intermediate position after the lancet moves to the extended position. The lancet is not shown in cross-section. The arrangement for guiding the lancet is shown in cross-section.

FIG. 15 shows a fourth non-limiting embodiment of a lancet device or lancet device portion of a meter, e.g., a blood glucose monitoring meter. The device also has a meter portion MP which can be of any type whether conventional or otherwise and which details are generally known and therefore not shown. The device also has a lancet device or lancet device portion LDP. The lancet device portion LDP has a body 100 which can be made as a one-piece member with the body of the meter portion MP or alternatively as a two-piece body made up of two body parts which are connected together (e.g., via a seam line SL as shown in FIG. 10). Such body parts can, of course, be connected, e.g., using adhesives and/or fasteners and/or welding and/or snap-together holding mechanisms (not shown) to each other when the lancet device LDP is initially assembled. A holding member 50 is movably disposed within the body 100. Additionally, a guiding support member 100a is fixed within the body 100 and functions to guide the lineal movement of the lancet L'. A front cover 2000 is removably connected or attached to an end of the body 100. By removing the front cover 2000, a user can gain access to the lancet L'. The lancet L' can thus be removed and replaced with a new lancet L', as needed, once the front cover 2000 is removed. As in known lancet devices, the lancet device LDP defines a plane P which is configured to contact (i.e., be positioned against) a user's skin. Although not shown, the instant embodiment may also utilize an inwardly curved and/or an outwardly curved surface plane P beyond which the lancet need can extend. The guiding support 100a has a front portion that can be accessed by a user upon removal of the front cover in order to all for replacement of the lancet L'. The lancet L' slides within the body 100 and more specifically slides within the member 100a. As will be described in more detail later on, movement of the lancet L' rearwardly, causes the member 50 to retract until it reaches a spring loaded position (not shown). The lancet L' includes a needle N and can be removed and replaced with a new lancet, as is the case in many lancet devices. To ensure that lancet L' is securely (yet removably) retained within the lancet device LDP, the front portion of the member 100a includes a lancet holding opening which receives the lancet L' therein.

As can be seen in FIG. 15, the member 100a preferably has a spring 60 arranged therein. In this regard, the spring 60, which can be made of spring steel, functions to cause the holding member 50 and lancet L' to move towards the extended or puncturing position (see e.g., FIGS. 8 and 9). By way of one non-limiting example, the spring 60 may have a diameter of between approximately 3 mm and approximately 15 mm, a freelength of between approximately 5 mm and approximately 40 mm, and a wire size of between approximately 0.5 mm and 2 mm. This first spring 60 causes (and/or biases) the lancet L' to move towards an extended position once two oppositely arranged cocking/trigger mechanisms 9 are activated (causing the same movement as indicated by arrows in FIGS. 5 and 6). Each cocking/trigger mechanisms 9 is arranged on an opposite end of a push-button 7 and has a cylindrical portion that is surrounded by a second spring 8. Each cocking/trigger mechanism 9 has a tapered surface 9a configured to slidably engage with one of two oppositely arranged protruding projections $PP_1$ and $PP_2$ arranged on the lancet L'. In the position shown in FIG. 15, the tapered surfaces 9a have not yet engaged with the protruding projections $PP_1$ and $PP_2$ arranged on the lancet L'. Furthermore, each spring 8 is shown in an original or extended position and biases each push-button 7 and, of course, the cocking/trigger mechanism 9 which is fixed thereto, towards an original pre-cocking and pre-triggering position shown in FIG. 15.

In operation, when force is simultaneously applied to the oppositely arranged finger engaging push-buttons 7 (i.e., by a user moving her index-finger and a thumb towards each other), the tapered surfaces 9a move into contact with projecting portions $PP_1$ and $PP_2$. This engagement causes the lancet L' to progressively move away from the lancet opening LO which in turn compresses the spring 60. Eventually, this engagement reaches a maximum point (maximum compression of the spring 60 and maximum movement of the lancet L' away from the lancet opening LO. FIG. 15 shows the lancet L' in an original or inter mediate position from which such movement begins. At the maximum movement point, any further movement of the cocking/trigger mechanisms 9 causes or allows the spring 60 to release its energy and move the lancet L' towards the lancet opening LO (in the same way as shown in FIGS. 8 and 9). Eventually, this movement of members 9 reaches a maximum point (maximum compression of the springs 8 and maximum inward movement of the push-buttons 7).

The maximum movement of the lancet L' is characterized by the lancet needle N extending through the lancet opening LO and past the plane P to thereby cause a puncturing of a user's skin (in the same way as shown in FIGS. 8 and 9). The amount that the needle N projects past the plane P is determined, by way of non-limiting example, by contact between the proximal end of the lancet L' and the inside surface of the front cap 2000 (and more specifically full compression of the spring 2000d between these surfaces) in the area of the lancet opening LO and just behind the plane P. Of course, this maximum movement causing a puncturing of a user's skin (as exemplified by FIGS. 8 and 9) occurs for only a fraction of a second. Then, the spring 60 aided by a third spring 2000d will cause the lancet L' to move back to the intermediate position shown in FIG. 15. At this point, the user can remove his or her fingers from the push-buttons 7. Then, the springs 8 will automatically expand and cause the members 9 to move in a direction opposite to the direction of cocking and triggering until finally reaching the position shown in FIG. 15. This movement will cause underside surface 9b of members 9 to engage the projecting portions $PP_1$ and $PP_2$ by a small amount which, in turn, will cause the lancet L' to move towards the lancet opening LO. This amount of movement is small, however, and not sufficient to cause the needle N to move through the lancet opening LO. On the other hand, this movement of the lancet L' in response to movement of the members 9 back to the original position (see FIG. 15), can be prevented by configuring the members 9 with a deflecting portion shown in FIGS. 24-27 and/or 30-33. FIGS. 28 and 29 illustrate one non-limiting way in which this would occur using the cocking and triggering member shown in FIGS. 24-27.

The front cap 2000 has a generally rectangular configuration and utilizes a connecting flange area 2000a which is configured to releasably engage with a proximal end of the body 100. This can occur by way of locking projections, or any other way, whether conventional or otherwise, of releasably connecting the front cap 2000 to the body 100. Of course, if the front cap 2000 is round or circular, internal threads can be utilized on the inside surface of flange area 2000a so that the front cap 2000 can be threadably connected to the proximal end of the body 100. The front cap 2000 also has a guiding sleeve portion 2000b which is configured to guide (e.g., using sliding engagement) the linear movement of the lancet L' as it moves towards the lancet opening LO. The front cap 2000 additionally has two oppositely arranged guiding recesses 2000c which are each configured to guide (e.g., using sliding engagement) the linear movement of the projecting portions $PP_1$ and $PP_2$ as the lancet L' moves towards the lancet opening LO and prevents the lancet L' from rotating more than a predetermined amount. This, in turn, ensures that there is proper engagement between the projecting portions $PP_1$ and $PP_2$ and surfaces 9a. The amount that the needle N projects past the plane P can also be determined, by way of non-limiting example, by contact between the projecting portions $PP_1$ and $PP_2$ and the bottom surface of the recesses 2000c instead of (or in addition to) contact between proximal end of the lancet L' and the inside surface of the front cap 2000 in the area of the lancet opening LO and just behind the plane P. The front cap 2000 can preferably be made as a one-piece member or alternatively as a two-piece member made up of two parts which are connected together. The third spring 2000d causes the lancet L' and the holding member 50 to move back to the intermediate position shown in FIG. 15 and is arranged between the lancet L' and the bottom surface of the flange 2000b in the area of the lancet opening LO. The third spring 2000d also becomes compressed when the lancet L' and the holding member 50 move from a retracted position to a the fully extended position.

Figure 16:
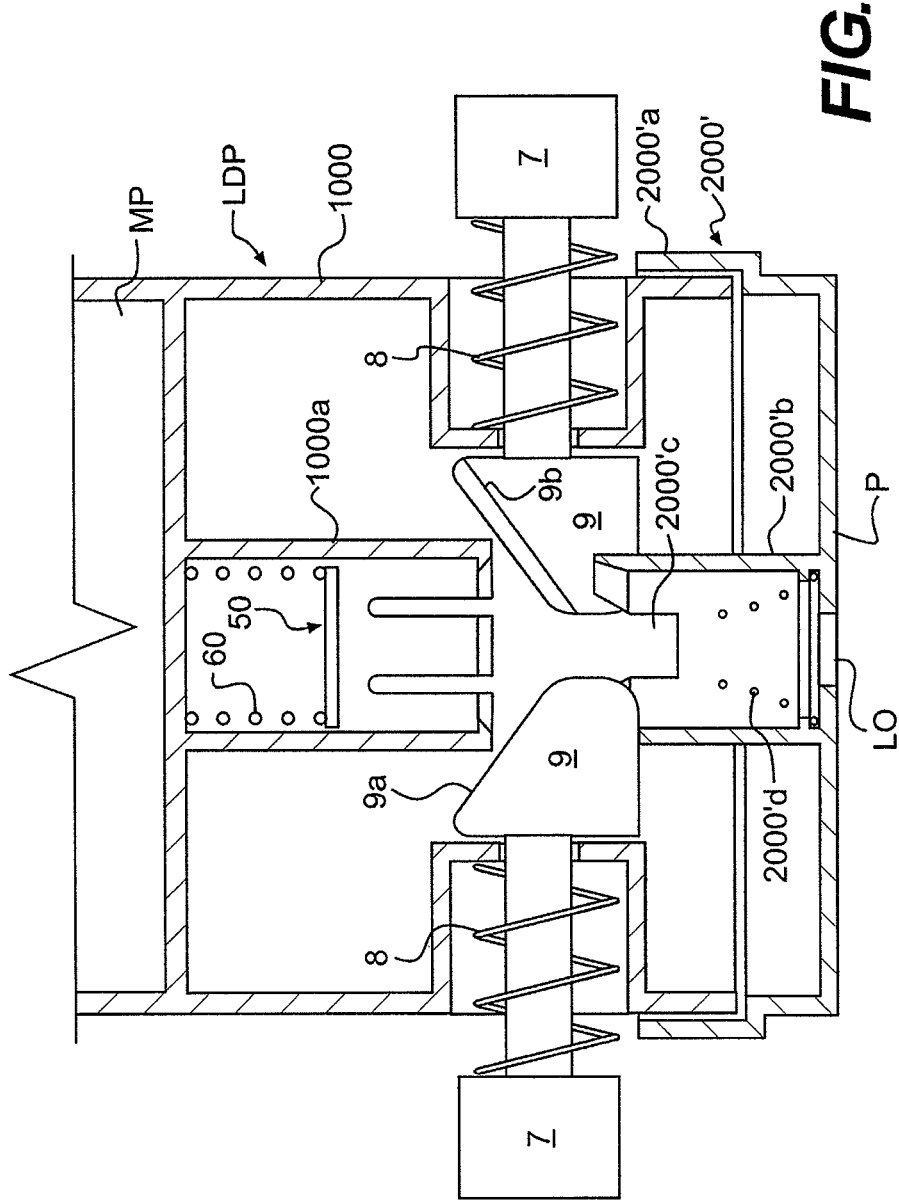
FIG. 16 shows a partial front side cross-section view of a fifth embodiment of the lancet device or lancet device portion of a meter. This embodiment utilizes a removable front cap that can adjust a depth or penetration of the lancet needle and a dual push-button trigger setting and/or cocking system and triggering system which is shown in non-cocking and non-triggering position. The front cap utilizes a spring to bias the lancet towards an intermediate position after the lancet moves to the extended position. The lancet is removed. The arrangement for guiding the lancet is shown in cross-section.

FIG. 16 shows a fifth non-limiting embodiment of a lancet device or lancet device portion of a meter, e.g., a blood glucose monitoring meter. The device also has a meter portion MP which can be of any type whether conventional or otherwise and which details are generally known and therefore not shown. The device also has a lancet device or lancet device portion LDP. The lancet device portion LDP has a body 1000 which can be made as a one-piece member with the body of the meter portion MP or alternatively as a two-piece body made up of two body parts which are connected together (e.g., via a seam line SL as shown in FIG. 10). Such body parts can, of course, be connected, e.g., using adhesives and/or fasteners and/or welding and/or snap-together holding mechanisms (not shown) to each other when the lancet device LDP is initially assembled. A holding member 50 is movably disposed within the body 1000. Additionally, a guiding support member 1000a is fixed within the body 1000 and functions to guide the linear movement of the lancet L' (not shown but similar to the lancet shown in FIG. 15). A front cover 2000' is removably connected or attached to an end of the body 1000. By removing the front cover 2000', a user can gain access to the lancet L'. The lancet L' can thus be removed and replaced with a new lancet L', as needed, once the front cover 2000' is removed. As in known lancet devices, the lancet device LDP defines a plane P which is configured to contact (i.e., be positioned against) a user's skin. Although not shown, the instant embodiment may also utilize an inwardly curved and/ or an outwardly curved surface plane P beyond which the lancet need can extend. The guiding support 1000a has a front portion that can be accessed by a user upon removal of the front cover in order to all for replacement of the lancet L'. The lancet L' slides within the body 1000 and more specifically slides within the member 1000a. As will be described in more detail later on, movement of the lancet L' rearwardly, causes the member 50 to retract until it reaches a spring loaded position (not shown). The lancet L' includes a needle N and can be removed and replaced with a new lancet, as is the case in many lancet devices. To ensure that lancet L' is securely (yet removably) retained within the lancet device LDP, the front portion of the member 1000a includes a lancet holding opening which receives the lancet L' therein.

As can be seen in FIG. 16, the member 1000a preferably has a spring 60 arranged therein. In this regard, the spring 60, which can be made of spring steel, functions to cause the holding member 50 and lancet L' to move towards the extended or puncturing position (see e.g., FIGS. 8 and 9). By way of one non-limiting example, the spring 60 may have a diameter of between approximately 3 mm and approximately 15 mm, a freelength of between approximately 5 mm and approximately 40 mm, and a wire size of between approximately 0.5 mm and 2 mm. This first spring 60 causes (and/or biases) the lancet L' to move towards an extended position once two oppositely arranged cocking/trigger mechanisms 9 are activated (causing the same movement as indicated by arrows in FIGS. 5 and 6). Each cocking/trigger mechanisms 9 is arranged on an opposite end of a push-button 7 and has a cylindrical portion that is surrounded by a second spring 8. Each cocking/trigger mechanism 9 has a tapered surface 9a configured to slidably engage with one of two oppositely arranged protruding projections $PP_1$ and $PP_2$ arranged on the lancet L'. In the position shown in FIG. 16, the tapered surfaces 9a have not yet engaged with the protruding projections $PP_1$ and $PP_2$ arranged on the lancet L'. Furthermore, each spring 8 is shown in an original or extended position and biases each push-button 7 and, of course, the cocking/trigger mechanism 9 which is fixed thereto, towards an original pre-cocking and pre-triggering position shown in FIG. 16.

In operation, when force is simultaneously applied to the oppositely arranged finger engaging push-buttons 7 (i.e., by a user moving her index-finger and a thumb towards each other), the tapered surfaces 9a move into contact with projecting portions $PP_1$ and $PP_2$ (not shown). This engagement causes the lancet L' to progressively move away from the lancet opening LO which in turn compresses the spring 60. Eventually, this engagement reaches a maximum point (maximum compression of the spring 60 and maximum movement of the lancet L' away from the lancet opening LO. FIG. 16 shows the lancet L' in an original or intermediate position from which such movement begins. At the maximum movement point, any further movement of the cocking/trigger mechanisms 9 causes or allows the spring 60 to release its energy and move the lancet L' towards the lancet opening LO (in the same way as shown in FIGS. 8 and 9). Eventually, this movement of members 9 reaches a maximum point (maximum compression of the springs 8 and maximum inward movement of the push-buttons 7).

The maximum movement of the lancet L' is characterized by the lancet needle N extending through the lancet opening LO and past the plane P to thereby cause a puncturing of a user's skin (in the same way as shown in FIGS. 8 and 9). The amount that the needle N projects past the plane P is determined, by way of non-limiting example, by contact between the proximal end of the lancet L' and the inside surface of the cap 2000' (and more specifically full compression of the spring 2000'd between these surfaces) in the area of the lancet opening LO and just behind the plane P. Of course, this maximum movement causing a puncturing of a user's skin (as exemplified by FIGS. 8 and 9) occurs for only a fraction of a second. Then, the spring 60 aided by a third spring 2000'd will cause the lancet L' to move back to an intermediate position. At this point, the user can remove his or her fingers from the push-buttons 7. Then, the springs 8 will automatically expand and cause the members 9 to move in a direction opposite to the direction of cocking and triggering until finally reaching the position shown in FIG. 15. This movement will cause underside surface 9b of members 9 to engage the projecting portions $PP_1$ and $PP_2$ by a small amount which, in turn, will cause the lancet L' to move towards the lancet opening LO. This amount of movement is small, however, and not sufficient to cause the needle N to move through the lancet opening LO. On the other hand, this movement of the lancet L' in response to movement of the members 9 back to the original position (see FIG. 16), can be prevented by configuring the members 9 with a deflecting portion shown in FIGS. 24-27 and/or 30-33. FIGS. 28 and 29 illustrate one non-limiting way in which this would occur using the cocking and triggering member shown in FIGS. 24-27.

The front cap 2000' preferably has a generally circular configuration and utilizes a connecting flange area 2000'a which is configured to releasably engage with a proximal end of the body 1000 which also preferably has a circular configuration at least in the area which will connect to area 2000'a. This can occur by way of locking projections, or any other way, whether conventional or otherwise, of releasably connecting the front cap 2000' to the body 1000. However, it is preferred that internal threads (or a cam engagement action) be utilized on the inside surface of flange area 2000'a so that the front cap 2000' can be adjustably and rotatably connected to the proximal end of the body 1000. The front cap 2000' also has a guiding sleeve portion 2000'b which is configured to guide (e.g., using sliding engagement) the linear movement of the lancet L' as it moves towards the lancet opening LO. The front cap 2000' additionally has two oppositely arranged guiding recesses 2000'c which are each configured to guide (e.g., using sliding engagement) the linear movement of the projecting portions $PP_1$ and $PP_2$ as the lancet L' moves towards the lancet opening LO and prevents the lancet L' from rotating more than a predetermined amount. This, in turn, ensures that there is proper engagement between the projecting portions $PP_1$ and $PP_2$ and surfaces 9a. The amount that the needle N projects past the plane P can also be determined, by way of non-limiting example, by contact between the projecting portions $PP_1$ and $PP_2$ and the bottom surface of the recesses 2000'c instead of (or in addition to) contact between proximal end of the lancet L' and the inside surface of the front cap 2000' in the area of the lancet opening LO and just behind the plane P. The front cap 2000' can preferably be made as a one-piece member or alternatively as a two-piece member made up of two parts which are connected together. The third spring 2000'd has one fixed to the front cap 2000' and causes the lancet L' and the holding member 50 to move back to the intermediate position shown in FIG. 16 and is arranged between the lancet L' and the bottom surface of the flange 2000'*b* in the area of the lancet opening LO. The third spring 2000'*d* also becomes compressed when the lancet L' and the holding member 50 move from a retracted position to a the fully extended position.

Figure 17:
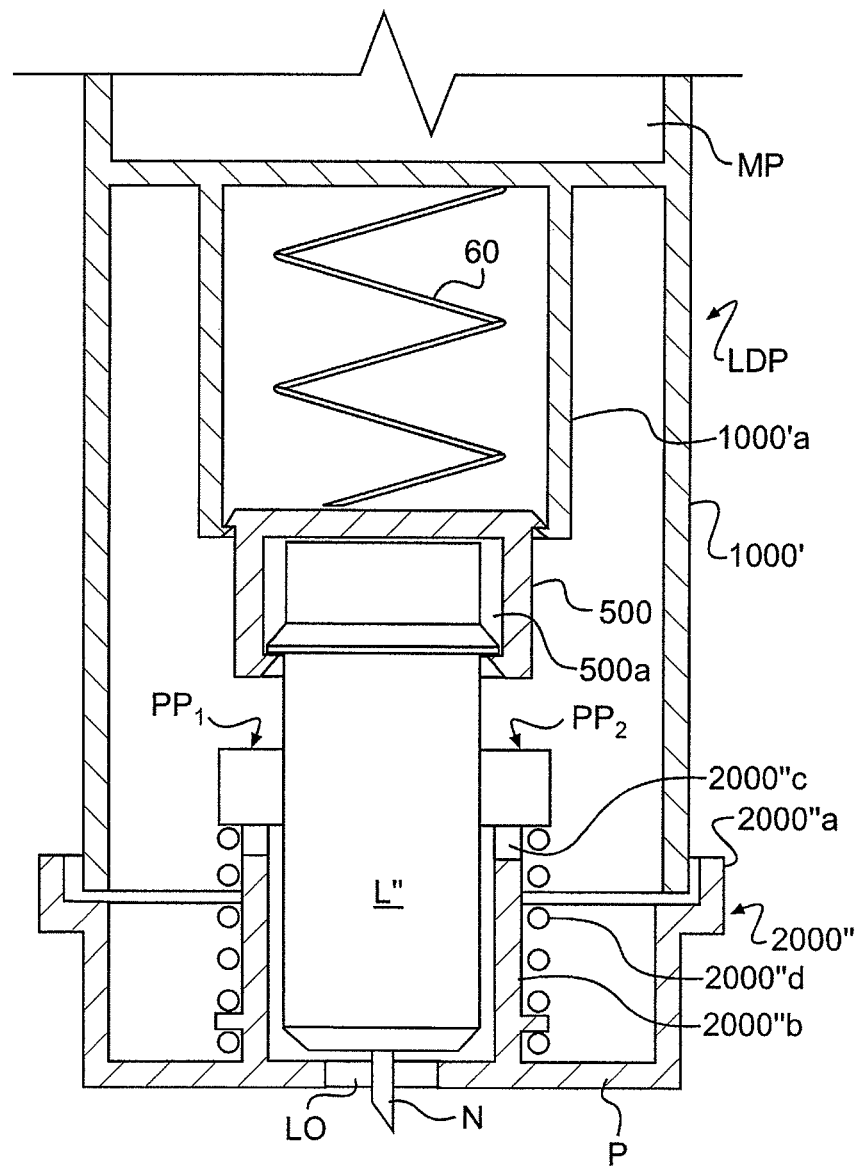
FIG. 17 shows a partial right-side cross-section view of a sixth embodiment of the lancet device or lancet device portion of a meter. This embodiment utilizes a removable front cap and a dual push-button trigger setting and/or cocking system and triggering system which is not shown for purposes of clarity. The front cap utilizes a spring to bias the lancet towards an intermediate position after the lancet moves to the extended position. The lancet is not shown in cross-section and is shown in the extended position. The arrangement for guiding the lancet holding member is shown in cross-section.

FIG. 17 shows a sixth non-limiting embodiment of a lancet device or lancet device portion of a meter, e.g., a blood glucose monitoring meter. The device also has a meter portion MP which can be of any type whether conventional or otherwise and which details are generally known and therefore not shown. The device also has a lancet device or lancet device portion LDP. The lancet device portion LDP has a body 1000' which can be made as a one-piece member with the body of the meter portion MP or alternatively as a two-piece body made up of two body parts which are connected together (e.g., via a seam line SL as shown in FIG. 10). Such body parts can, of course, be connected, e.g., using adhesives and/or fasteners and/or welding and/or snap-together holding mechanisms (not shown) to each other when the lancet device LDP is initially assembled. A holding member 500 is movably disposed within the body 1000'. Additionally, a guiding support member 1000'*a* is fixed within the body 1000' and functions to guide the linear movement of the holding member 500. A front cover 2000" is removably connected or attached to an end of the body 1000'. By removing the front cover 2000", a user can gain access to the lancet L". The lancet L" can thus be removed and replaced with a new lancet L", as needed, once the front cover 2000" is removed. As in known lancet devices, the lancet device LDP defines a plane P which is configured to contact (i.e., be positioned against) a user's skin. Although not shown, the instant embodiment may also utilize an inwardly curved and/or an outwardly curved surface plane P beyond which the lancet need can extend. The holding member 500 has a front portion that can be accessed by a user upon removal of the front cover 2000" in order to all for replacement of the lancet L". The lancet L" slides within the body 1000' and more specifically slides with the holding member 500 within support 1000'*a*. As will be described in more detail later on, movement of the lancet L" rearwardly, causes the member 500 to retract into member 1000'*a* until it reaches a spring loaded position (not shown). The lancet L" includes a needle N and can be removed and replaced with a new lancet, as is the case in many lancet devices. To ensure that lancet L" is securely (yet removably) retained within the lancet device LDP, the front portion of the holding member 500 includes a lancet holding opening 500*a* which receives the lancet L' therein.

As can also be seen in FIG. 17, the member 1000'*a* preferably has a spring 60 arranged therein. In this regard, the spring 60, which can be made of spring steel, functions to cause the holding member 500 and lancet L" to move towards the extended or puncturing position (as shown FIG. 17). By way of one non-limiting example, the spring 60 may have a diameter of between approximately 3 mm and approximately 15 mm, a freelength of between approximately 5 mm and approximately 40 mm, and a wire size of between approximately 0.5 mm and 2 mm. This first spring 60 causes (and/or biases) the lancet L" to move towards an extended position once two oppositely arranged cocking/trigger mechanisms (not shown but similar to arrangements 7/8/9 shown in FIG. 16). Each cocking/trigger mechanisms is arranged on an opposite end of a push-button and has a cylindrical portion that is surrounded by a second spring. Each cocking/trigger mechanism has a tapered surface configured to slidably engage with one of two oppositely arranged protruding projections $PP_1$ and $PP_2$ arranged on the lancet L". In the position shown in FIG. 17, the tapered surfaces have already engaged with the protruding projections $PP_1$ and $PP_2$ arranged on the lancet L". Furthermore, each spring (e.g., spring 8 shown in FIG. 16) biases each push-button and, of course, the cocking/trigger mechanism which is fixed thereto, towards an original pre-cocking and pre-triggering position.

In operation, when force is simultaneously applied to the oppositely arranged finger engaging push-buttons (i.e., by a user moving her index-finger and a thumb towards each other), the tapered surfaces (e.g., tapered surfaces 9*a* as shown in FIG. 16) move into contact with projecting portions $PP_1$ and $PP_2$. This engagement causes the lancet L" to progressively move away from the lancet opening LO which in turn compresses the spring 60. Eventually, this engagement reaches a maximum point (maximum compression of the spring 60 and maximum movement of the lancet L" away from the lancet opening LO. FIG. 17 shows the lancet L" in the fully extended or puncturing position after the maximum point was reached. At the maximum movement point, any further movement of the cocking/trigger mechanisms causes or allows the spring 60 to release its energy and move the lancet L" towards the lancet opening LO (FIG. 17). Eventually, this movement of members (e.g., similar to members 9 shown in FIG. 16) reaches a maximum point (maximum compression of the springs 8 and maximum inward movement of the push-buttons 7).

The maximum movement of the lancet L" is characterized by the lancet needle N extending through the lancet opening LO and past the plane P to thereby cause a puncturing of a user's skin (the puncturing position is shown in FIG. 17). The amount that the needle N projects past the plane P is determined, by way of non-limiting example, by contact between the proximal end of the lancet L" and the inside surface of the cap 2000" in the area of the lancet opening LO and just behind the plane P. Of course, this maximum movement causing a puncturing of a user's skin occurs for only a fraction of a second. Then, the spring 60 aided (optionally by a third spring) will cause the lancet L" to move back to the intermediate. At this point, the user can remove his or her fingers from the push-buttons. Then, the springs will automatically expand and cause the members to move in a direction opposite to the direction of cocking and triggering until finally reaching an original position (similar to that shown in FIG. 15). As was the case in FIG. 15, this movement will cause underside surface 9*b* of members 9 to engage the projecting portions $PP_1$ and $PP_2$ by a small amount which, in turn, will cause the lancet L" to move towards the lancet opening LO. This amount of movement is small, however, and not sufficient to cause the needle N to move through the lancet opening LO. On the other hand, this movement of the lancet L" in response to movement of the members 9 back to the original position (see FIG. 15), can be prevented by configuring the members 9 with a deflecting portion shown in FIGS. 24-27 and/or 30-33. FIGS. 28 and 29 illustrate one non-limiting way in which this would occur using the cocking and triggering member shown in FIGS. 24-27.

Figure 18:
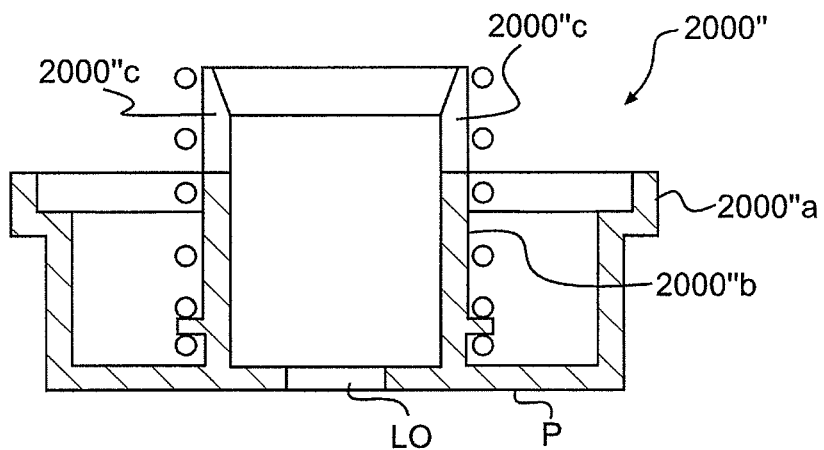
FIG. 18 shows a front side cross-section view of the front cap used in the embodiment shown in FIG. 17.
Figure 19:
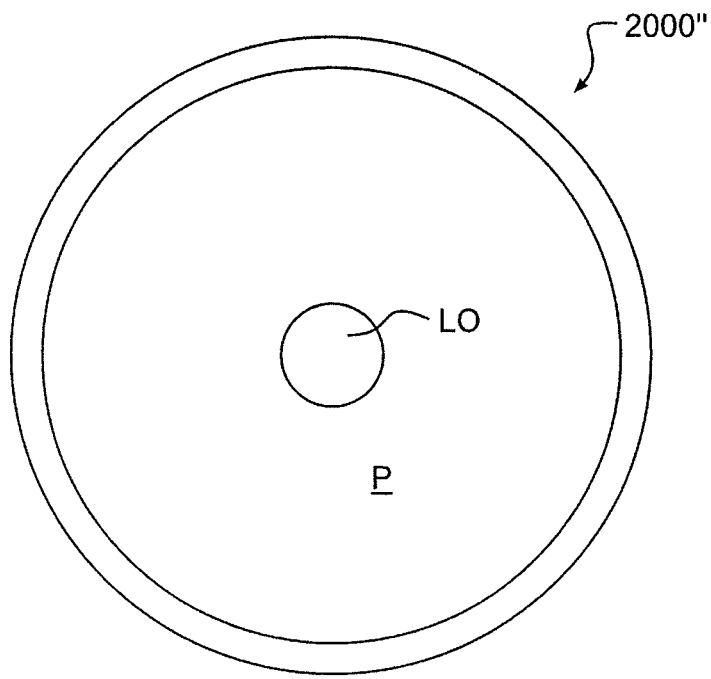
FIG. 19 shows a bottom side view of the front cap shown in FIG. 18.
Figure 20:
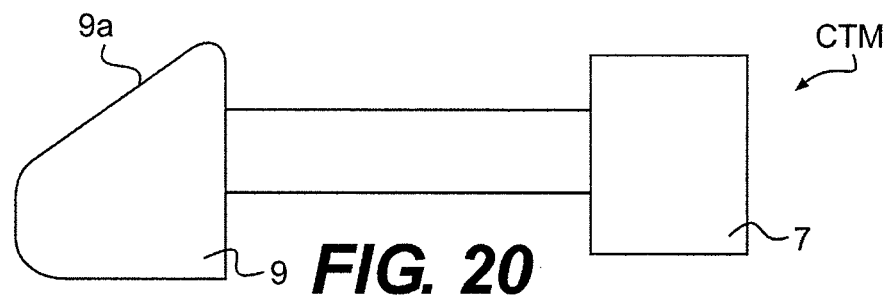
FIG. 20 shows a rear side view of the push-button cocking and triggering member which can be used in one or more of the embodiments shown in FIGS. 1-19.
Figure 21:
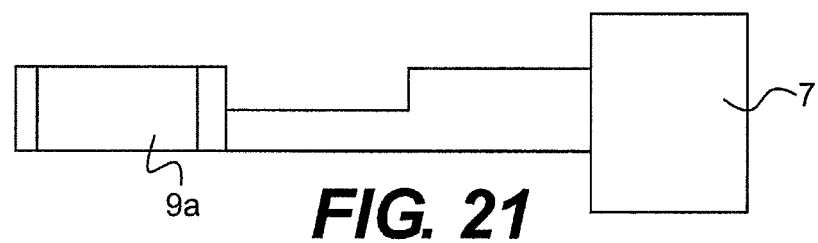
FIG. 21 shows a top view of FIG. 20.
Figure 22:
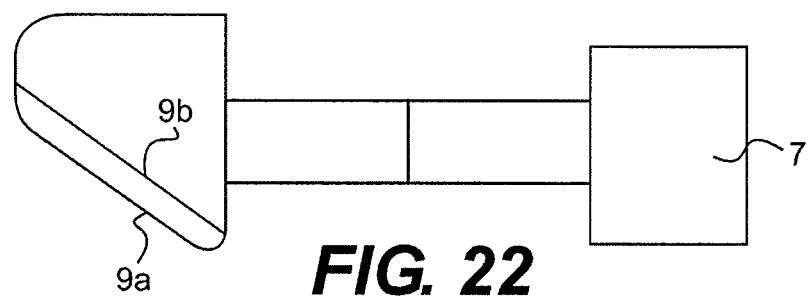
FIG. 22 shows an opposite side view of FIG. 20.
Figure 23:
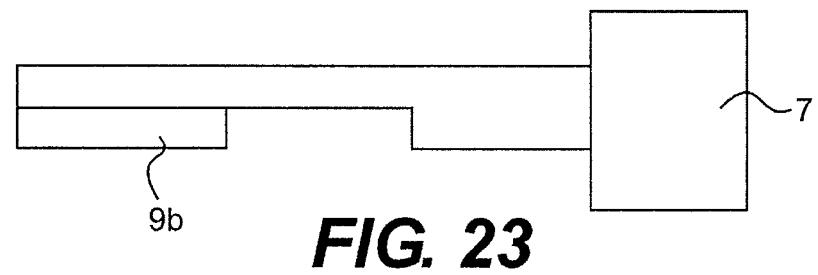
FIG. 23 shows an opposite side view of FIG. 21.
Figure 24:
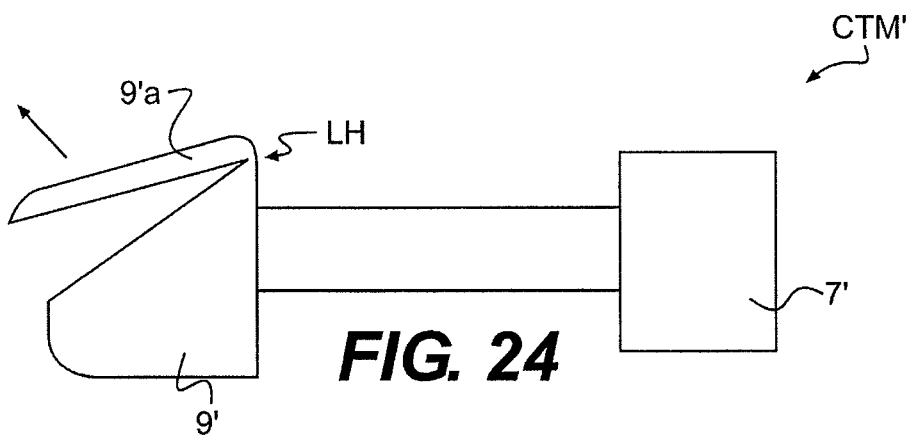
FIG. 24 shows a rear side view of another embodiment of the push-button cocking and triggering member which can be used in one or more of the embodiments shown in FIGS. 1-19.
Figure 25:
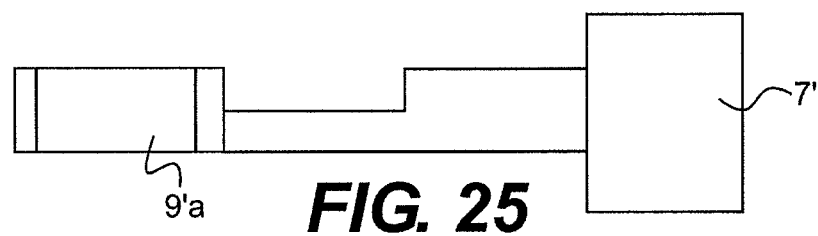
FIG. 25 shows a top view of FIG. 24.
Figure 26:
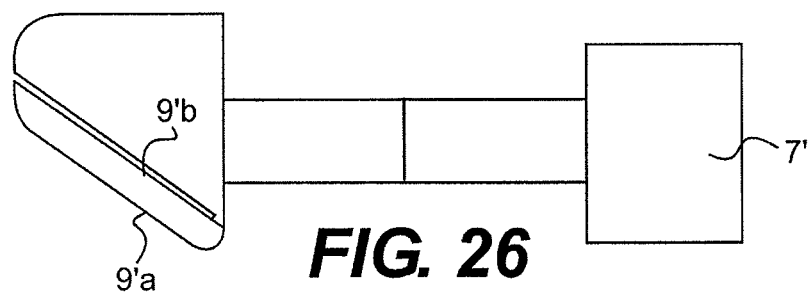
FIG. 26 shows an opposite side view of FIG. 24.
Figure 27:
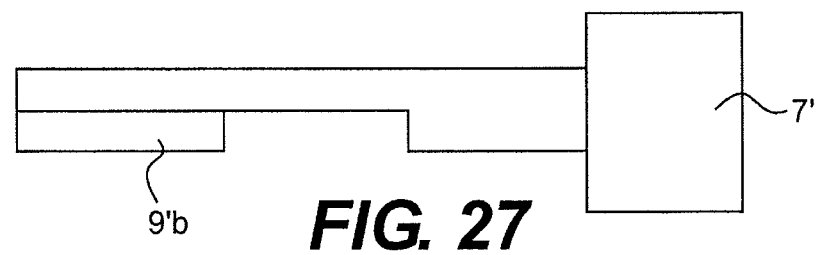
FIG. 27 shows an opposite side view of FIG. 25.

As is shown in FIGS. 18 and 19, the front cap 2000" preferably has a generally circular configuration and utilizes a connecting flange area 2000"*a* which is configured to releasably engage with a proximal end of the body 1000' which also preferably has a circular configuration at least in the area which will connect to area 2000"*a*. This can occur by way of locking projections, or any other way, whether conventional or otherwise, of releasably connecting the front cap 2000" to the body 1000'. However, it is preferred that internal threads (or a cam engagement action) be utilized on the inside surface of flange area 2000"*a* so that the front cap 2000" can be adjustably and rotatably connected to the proximal end of the body 1000'. The front cap 2000" also has a guiding sleeve portion 2000"*b* which is configured to guide (e.g., using sliding engagement) the linear movement of the lancet L" as it moves towards the lancet opening LO. The front cap 2000" additionally has two oppositely arranged guiding recesses 2000"*c* which are each configured to guide (e.g., using sliding engagement) the linear movement of the projecting portions $PP_1$ and $PP_2$ as the lancet L" moves towards the lancet opening LO and prevents the lancet L" from rotating more than a predetermined amount. This, in turn, ensures that there is proper engagement between the projecting portions $PP_1$ and $PP_2$ and surfaces 9*a*. The amount that the needle N projects past the plane P can also be determined, by way of non-limiting example, by contact between the projecting portions $PP_1$ and $PP_2$ and the bottom surface of the recesses 2000"*c* instead of (or in addition to) contact between proximal end of the lancet L" and the inside surface of the front cap 2000" in the area of the lancet opening LO and just behind the plane P. The front cap 2000" can preferably be made as a one-piece member or alternatively as a two-piece member made up of two parts which are connected together. A third spring 2000"*d* is utilized on the front cap 2000" for causing the lancet L" and the holding member 500 to move back to the intermediate position and is arranged between the projecting portions $PP_1$ and $PP_2$ of the lancet L" and the bottom outer projecting flange of the flange 2000"*b* in the area of the lancet opening LO. The third spring 2000"*d* also becomes compressed when the lancet L" and the holding member 500 move from a retracted position to a the fully extended position.

FIGS. 20-23 show various views of the push-button cocking and triggering member CTM which can be used in one or more of the embodiments disclosed herein. The member CTM has a member 9 which includes a tapered engaging surface 9*a* that engages a projecting portion PP of the lancet (or lancet holding member) during the cocking and triggering movement and an angled underside surface 9*b* which engages (by a small amount) the projecting portion PP during a reverse movement. The member CTM also utilizes a push-button portion 7 which is configured to be engaged by a user's finger.

FIGS. 24-27 show various views of an alternative push-button cocking and triggering member CTM' which can be used in one or more of the embodiments disclosed herein. The member CTM' has a member 9' which includes a tapered engaging surface 9'*a* that engages a projecting portion PP of the lancet (or lancet holding member) during the cocking and triggering movement and an angled underside surface 9'*b* which engages (by a small amount) the projecting portion PP during a reverse movement. The member CTM' also utilizes a push-button portion 7' which is configured to be engaged by a user's finger. The engaging surfaces 9'*a* and 9'*b* are arranged on a deflectable element which is connected to the main portion of the member 9' via a living hinge LH.

FIGS. 30-33 show various views of an alternative push-button cocking and triggering member CTM" which can be used in one or more of the embodiments disclosed herein. The member CTM" has a member 9" which includes a tapered engaging surface 9"*a* that engages a projecting portion PP of the lancet (or lancet holding member) during the cocking and triggering movement and an angled underside surface 9"*b* which engages (by a small amount) the projecting portion PP during a reverse movement. The member CTM" also utilizes a push-button portion 7" which is configured to be engaged by a user's finger. At least a portion of the engaging surfaces 9"*a* and 9"*b* are arranged on a deflectable element which is connected to the main portion of the member 9" via a living hinge LH'.

Figure 34:
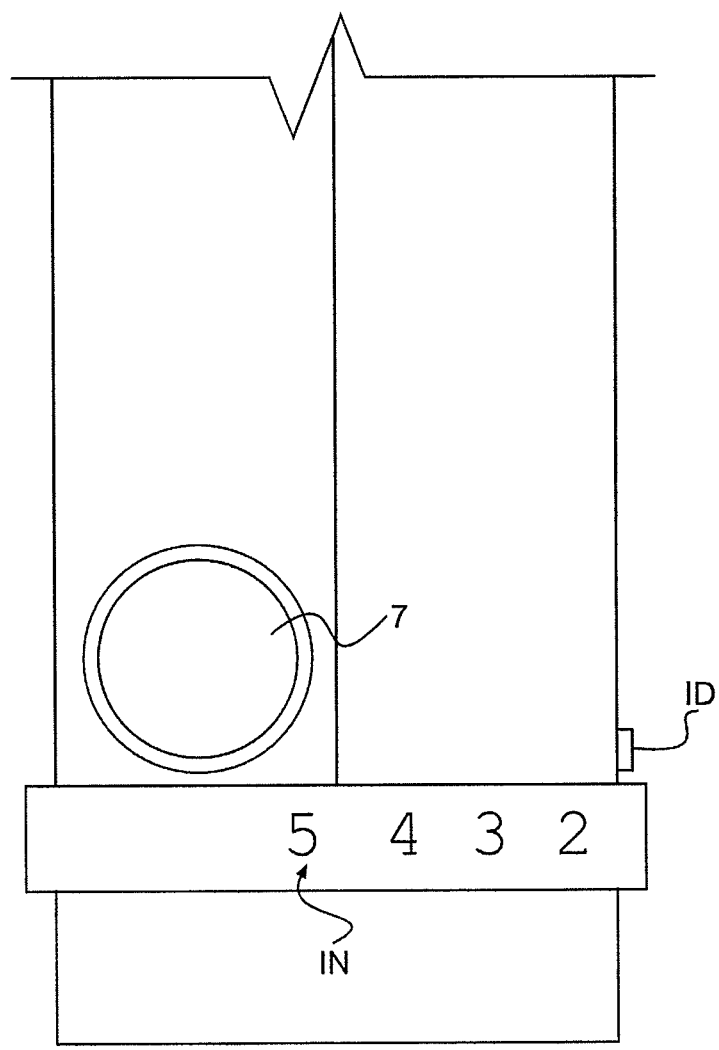
FIG. 34 shows a right side view of another embodiment of the lancet device or lancet device portion of a meter. This embodiment utilizes a depth-setting front cap with indicia and an indicator arranged on the body.

FIG. 34 shows a right side view of another embodiment of the lancet device or lancet device portion of a meter. This embodiment utilizes a depth-setting front cap with indicia IN and an indicator ID arranged on the body. Rotation of the front cap in one direction causes the front cap to move axially relative to the body. This feature is known in the art and will therefore not be described in detail herein.

Figure 35:
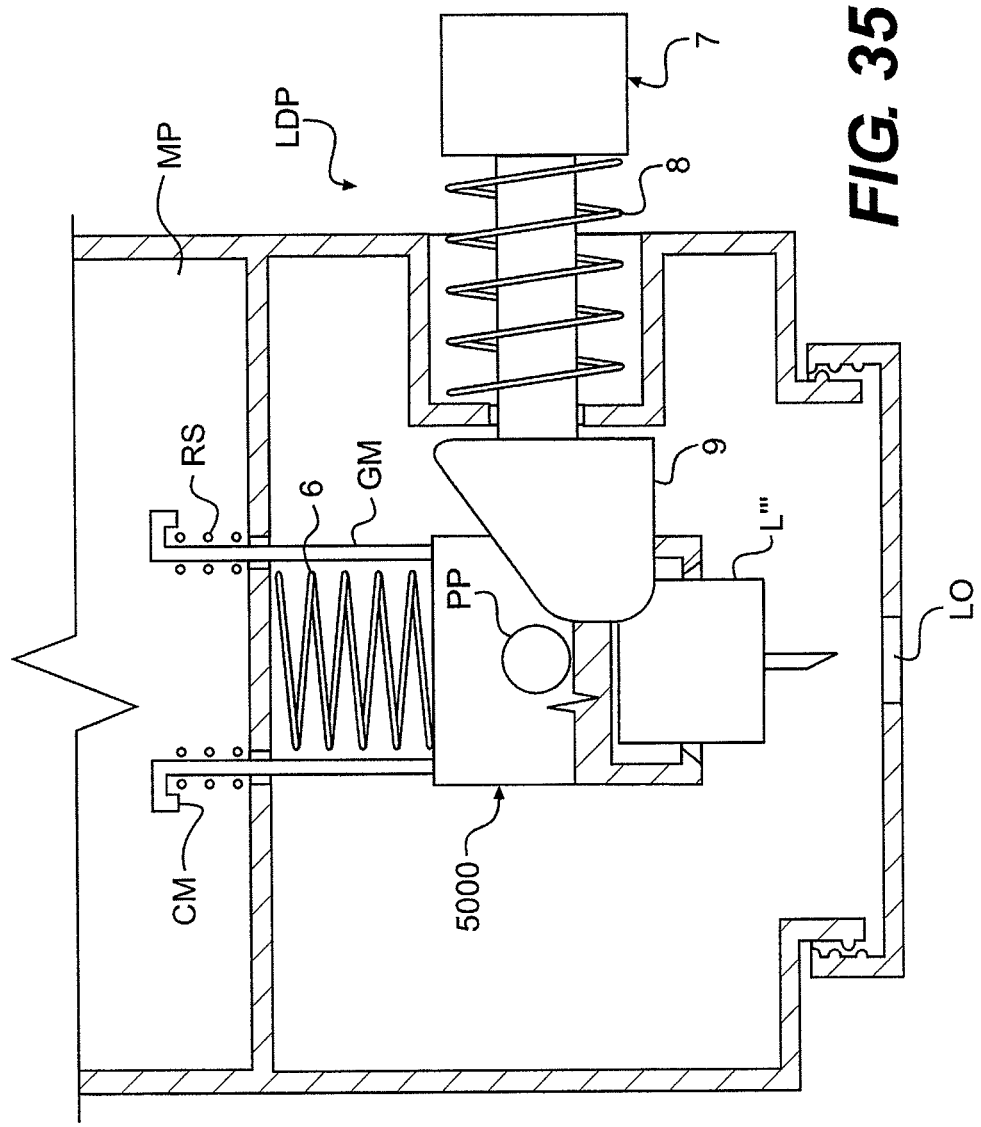
FIG. 35 shows a front side cross-section view of another embodiment of the lancet device or lancet device portion of a meter. This embodiment utilizes a depth-setting front cap and a lancet holding member. The lancet holding member is shown in partial cross-section. The push-button cocking and triggering member used in this embodiment engages with a protruding from the lancet holding member whose movement is guided by guide members and which is moved back to an initial or intermediate position by return springs mounted to the guide members.

FIG. 35 shows a front side cross-section view of another embodiment of the lancet device or lancet device portion of a meter. This embodiment utilizes a depth-setting front cap of the type shown in FIG. 34 and a lancet holding member 5000 that receives therein a lancet L'" and that is movably guided by guide members GM. Two retracting springs RS are mounted to the guide members GM and function to move the lancet holding member 5000 back from the extended or puncturing position. Each guide member GM has a contact member CM which limits (by contacting a wall of the body through which the members GM penetrate) the maximum movement of the holding member 5000 towards the extended or puncturing position. The device otherwise functions in a manner similar to many of the devices previously described. Although not shown, the device shown in FIG. 35 can also utilize two members 7/8/9 (similar to the embodiments shown in e.g., FIGS. 15 and 16) instead of just one.

Figure 36:
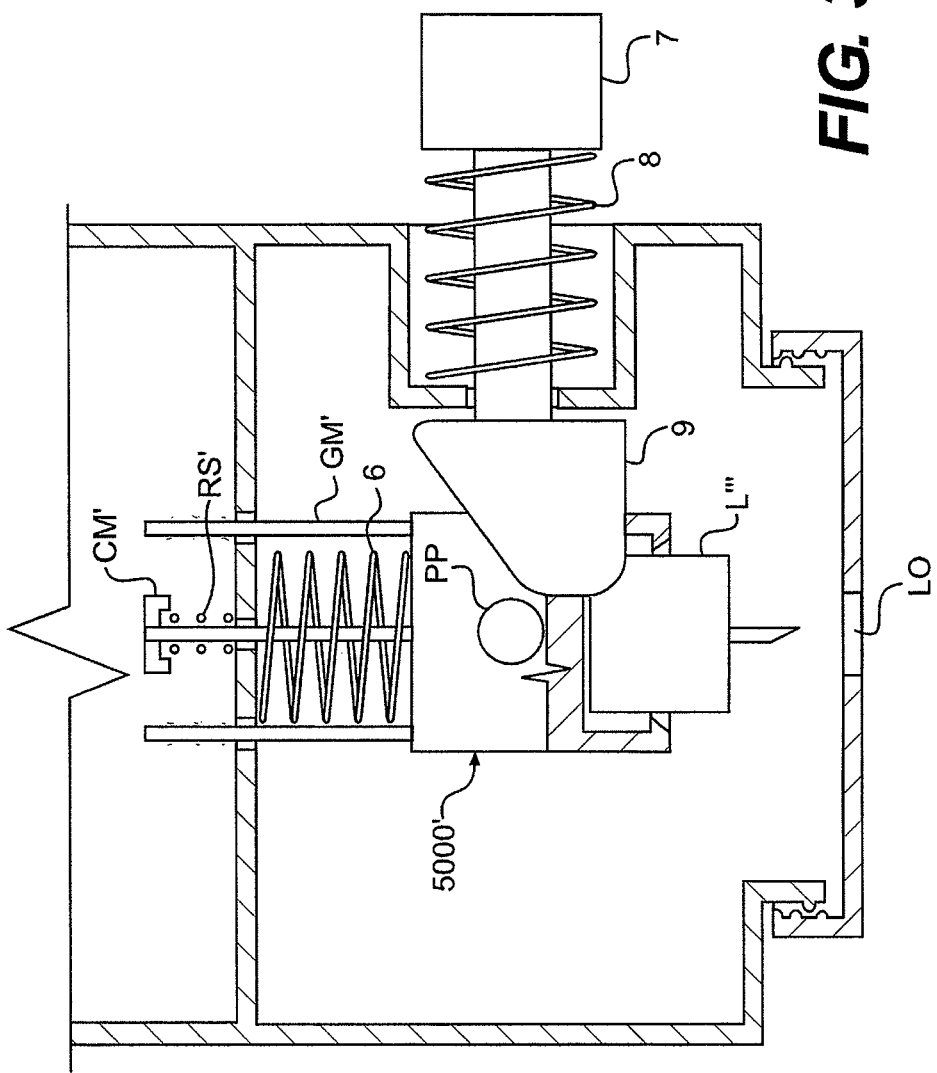
FIG. 36 shows a front side cross-section view of another embodiment of the lancet device or lancet device portion of a meter. This embodiment utilizes a depth-setting front cap and a lancet holding member. The lancet holding member is shown in partial cross-section. The push-button cocking and triggering member used in this embodiment engages with a protruding from the lancet holding member whose movement is guided by guide members and which is moved back to an initial or intermediate position by a return spring.

FIG. 36 shows a front side cross-section view of another embodiment of the lancet device or lancet device portion of a meter. This embodiment utilizes a depth-setting front cap of the type shown in FIG. 34 and a lancet holding member 5000' that receives therein a lancet L'" and that is movably guided by guide members GM'. A retracting spring RS' is mounted to a centrally disposed guide member GM' and functions to move the lancet holding member 5000' back from the extended or puncturing position. The central guide member GM' has a contact member CM' which limits (by contacting a wall of the body through which the members GM' penetrate) the maximum movement of the holding member 5000' towards the extended or puncturing position. The device otherwise functions in a manner similar to many of the devices previously described. Although not shown, the device shown in FIG. 36 can also utilize two members 7/8/9 (similar to the embodiments shown in e.g., FIGS. 15 and 16) instead of just one.

Figure 37:
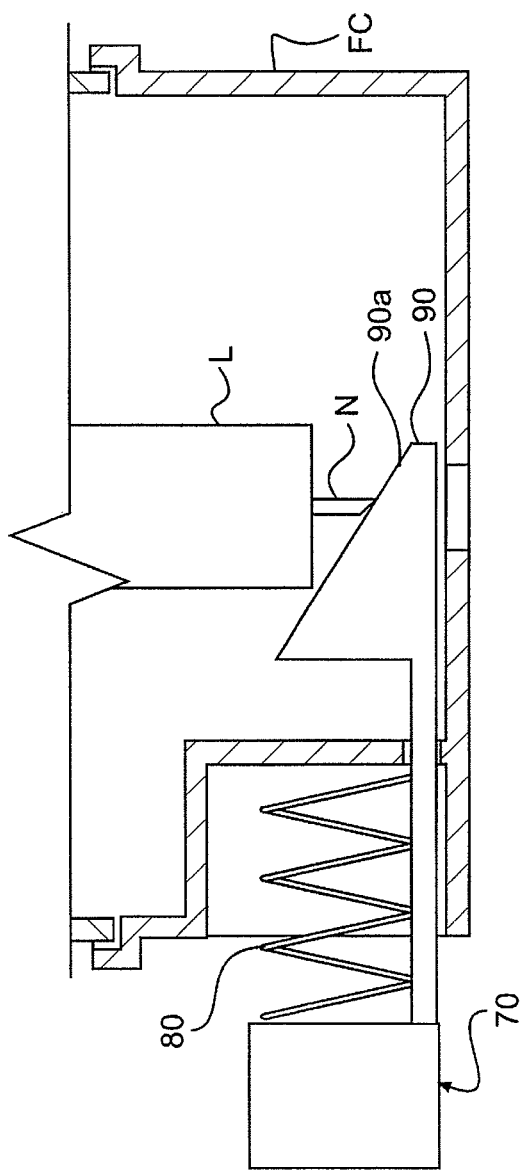
FIG. 37 shows a front side cross-section view of another embodiment of the lancet device or lancet device portion of a meter. This embodiment utilizes a front cap that utilizes the push-button cocking and triggering system. The push-button cocking and triggering member of the system engages with a front end of the lancet and, when moved, causes the lancet to move from an initial or intermediate position shown in FIG. 37.
Figure 38:
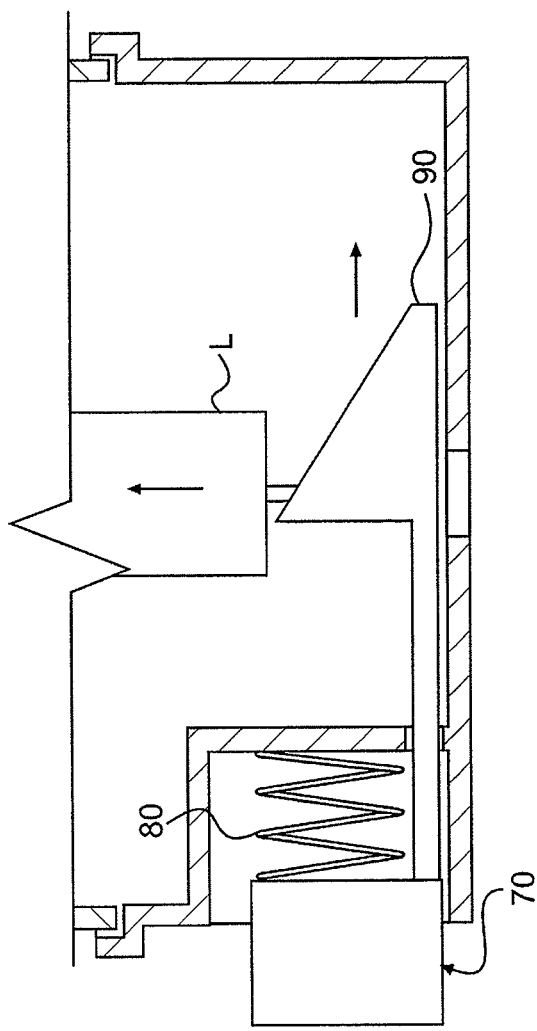
FIG. 38 shows another front side cross-section view of the embodiment of FIG. 37. The push-button cocking and triggering member has been moved to the point where it has caused the lancet to move from an initial or intermediate position shown in FIG. 37 to the retracted position shown in FIG. 38.
Figure 39:
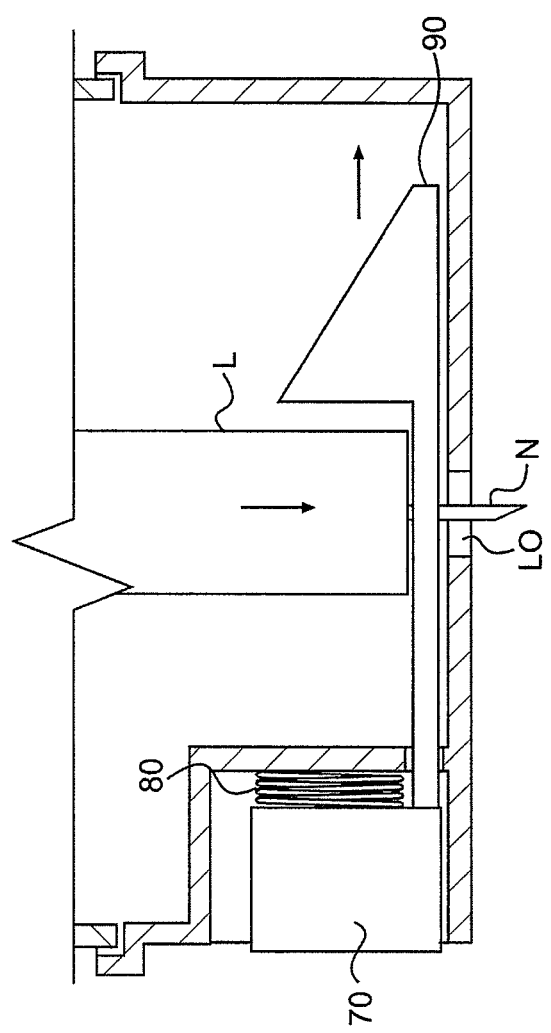
FIG. 39 shows another front side cross-section view of the embodiment of FIG. 37. The push-button cocking and triggering member has been moved to a point where it has caused the lancet to move from the retracted position shown in FIG. 38 to the extended or puncturing position shown in FIG. 39.
Figure 40:
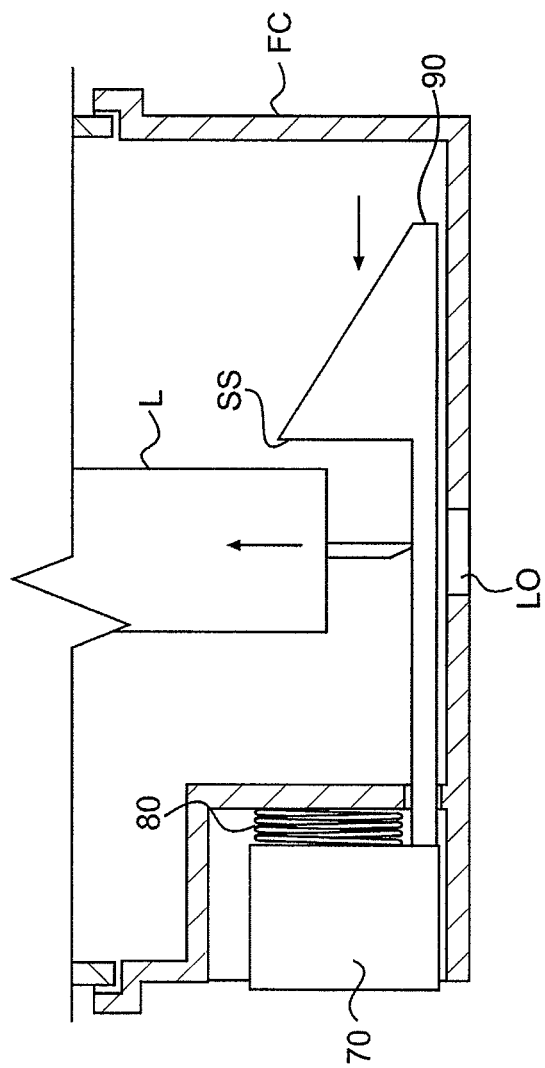
FIG. 40 shows another front side cross-section view of the embodiment of FIG. 37. The push-button cocking and triggering member has been moved to back towards an initial position but is prevented from doing so by the lancet which has moved back to an intermediate position from the extended or puncturing position shown in FIG. 39.

FIG. 37 shows a front side cross-section view of another embodiment of the lancet device or lancet device portion of a meter. This embodiment utilizes a front cap FC that utilizes the push-button cocking and triggering system. The push-button cocking and triggering member has an engaging portion 90 whose tapered surface 90*a* engages with a front end of the lancet L and, when moved, causes the lancet L to move from an initial or intermediate position shown in FIG. 37. A push-button portion 70 is configured to be engaged by a user's finger and is biased via a spring 80 towards an original position. In FIG. 38, the push-button cocking and triggering member 70/90 has been moved to the point where it has caused the lancet L to move from an initial or intermediate position shown in FIG. 37 to the retracted position shown in FIG. 38. In FIG. 39, the push-button cocking and triggering member 70/90 has been moved to a point where it has caused the lancet L to move from the retracted position shown in FIG. 38 to the extended or puncturing position shown in FIG. 39. In FIG. 40, the push-button cocking and triggering member 70/90 has been moved to back towards an initial position but is prevented from doing so by contact between the stop surface SS and the lancet L which has moved back to an intermediate position from the extended or puncturing position shown in FIG. 39. The user must then remove the front cap FC, should replace the lancet L with a new one, and must then re-install the front cap FC.

FIG. 41 shows a front side view of the push-button cocking and triggering member used in the embodiment shown in FIGS. 37-40 and FIG. 42 shows a top view of the push-button cocking and triggering member shown in FIG. 41.

Figure 43:
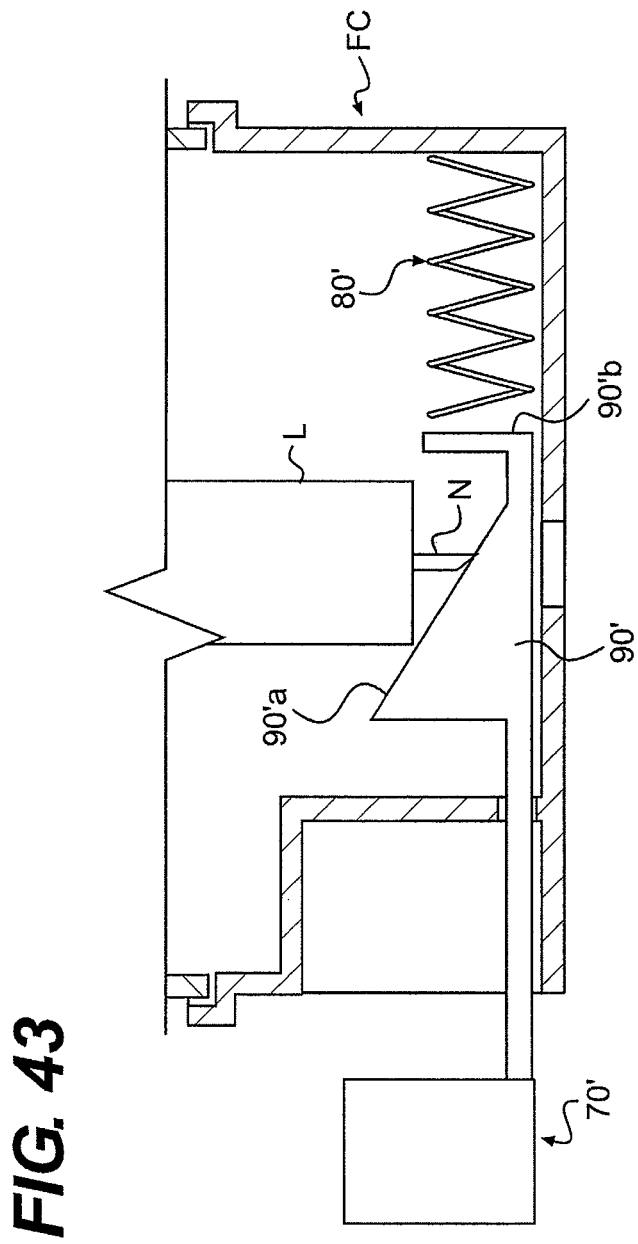
FIG. 43 shows a front side cross-section view of another embodiment of the lancet device or lancet device portion of a meter. This embodiment is similar to that of FIG. 37 except that the front end of engaging portion includes flanges which compress a spring when the push-button cocking and triggering system is moved inwardly.

FIG. 43 shows another embodiment of the lancet device or lancet device portion of a meter. This embodiment is similar to that of FIG. 37 except that the front end of engaging portion 90' includes flanges 90'b which compress a spring 80' when the push-button cocking and triggering system 70'/90' is moved inwardly.

Figure 44:
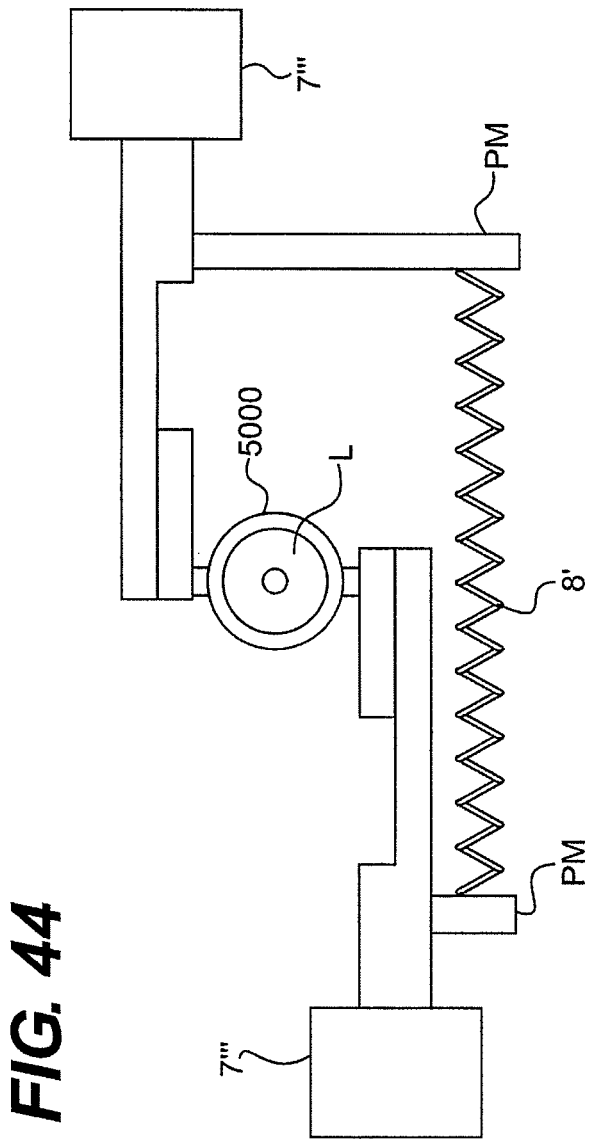
FIG. 44 schematically shows one non-limiting way in which the two-push button devices disclosed herein can utilize a single spring instead of two springs.

FIG. 44 schematically shows one non-limiting way in which the two-push button devices disclosed herein can utilize a single spring 8' instead of two springs. The spring 8' is compressed by protruding members PM extending out from the push button devices.

Figure 45:
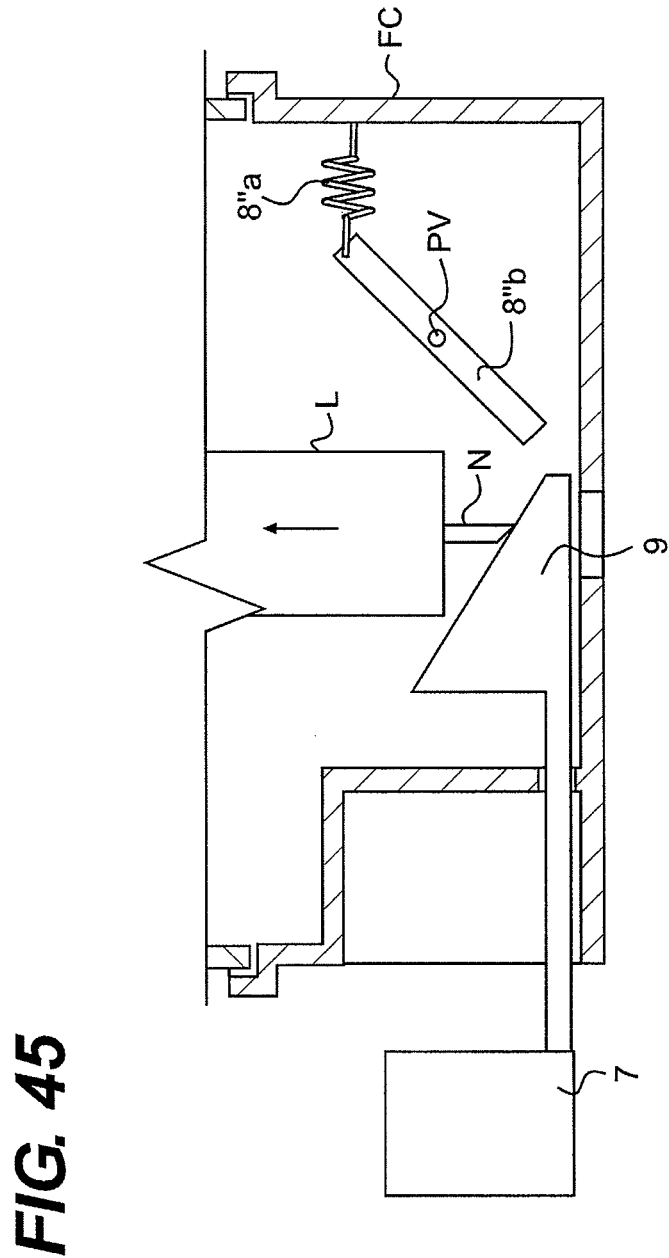
FIG. 45 shows a front side cross-section view of another embodiment of the lancet device or lancet device portion of a meter. This embodiment is similar to that of FIG. 37 except that the front end of engaging portion engages a pivotally mounted plate member which has an opposite end biased by a tension spring.

FIG. 45 shows another embodiment of the lancet device or lancet device portion of a meter. This embodiment is similar to that of FIG. 37 except that the front end of engaging portion engages a pivotally mounted plate member 8"b which has an opposite end biased by a tension spring 8"a.

Of course, the invention contemplates embodiments wherein the body and front cover have a non-circular shapes similar to that of U.S. Pat. No. 5,464,418 to SCHRAGA, the disclosure of which is hereby expressly incorporated by reference herein it its entirety. The invention also contemplates utilizing one or more of the lancet removal systems disclosed in pending U.S. patent application Ser. No. 11/548,618 (P30701) to SCHRAGA, the disclosure of which is hereby expressly incorporated by reference herein it its entirety.

The various parts, with the exception of the springs, can preferably be made as one-piece structures by e.g., injection molding. In this regard, they are preferably made of a plastic or synthetic resin such as, e.g., ABS plastic. The body and can also be made of ABS-Metallic Silver and have a finish designated as SPI-A2. The front cover and push-button may also be made of ABS-Light Blue and have a finish designated as SPI-A2. The holding member may also be made of Delrin-Natural and have a finish designated as SPI-C1. Of course, other materials and/or finishes may be utilized, without leaving the scope of the invention. Moreover, each part may even be made of a plurality of sections of parts which are joined together to form the complete parts, without leaving the scope of the invention. Thus, all the parts of the lancet device, with the exception of the springs (which can be made of spring steel) and with the exception of the lancet needle (which can be a conventional metal needle mounted to a conventional plastic lancet L), may be made from plastic materials and can be formed using conventional injection molding techniques or other known manufacturing methods. The front cap and/or body, for example, can be integrally formed with peripheral grooves and/or projections (similar to a coin), and with the indicating marks. However, when practical, other materials and manufacturing processes may also be utilized. Examples of desirable plastics include polypropylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN". The invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A multi-use lancet device comprising:
   a skin engaging end that includes a lancet opening through which a lancet needle may extend;
   at least one compression spring comprising one of;
      a center axis oriented parallel to an axis of the lancet opening; and/or
      a center axis oriented perpendicular to an axis of the lancet opening;
   a movably mounted holding member configured to receive a replaceable lancet;
   a combined triggering and cocking system associated with the at least one spring and being structured and arranged to move the holding member to a retracted position during a cocking phase and to cause the holding member to move to an extended position during a triggering phase; and
   a portion of the combined triggering and cocking system being located outside a housing of the lancet device and being located closer to the skin engaging end than the compression spring.

2. The lancet device of claim 1, wherein the combined triggering and cocking system is activated manually and automatically causes the holding member to move to the extended position during the triggering phase.

3. The lancet device of claim 1, wherein the combined triggering and cocking system performs the cocking phase before the triggering phase.

4. The lancet device of claim 1, wherein the combined triggering and cocking system activates the cocking phase and the triggering phase using linear movement.

5. The lancet device of claim 1, wherein the portion of the combined triggering and cocking system comprises at least one push-button.

6. The lancet device of claim 1, wherein the portion of the combined triggering and cocking system comprises at least one push-button mounted to one of two opposite sides of the lancet device.

7. The lancet device of claim 1, wherein the portion of the combined triggering and cocking system comprises two push-buttons mounted to opposite sides of the lancet device.

8. The lancet device of claim 1, wherein the portion of the combined triggering and cocking system comprises a push-button biased towards an extended position.

9. The lancet device of claim 1, wherein the portion of the combined triggering and cocking system comprises at least one push-button biased towards an extended position and movable towards a central axis of the holding member.

10. The lancet device of claim 1, wherein the lancet device comprises a meter lancet device.

11. The lancet device of claim 1, wherein the lancet device comprises a blood glucose monitoring system.

12. The lancet device of claim 1, wherein the lancet device comprises a blood glucose meter.

13. The lancet device of claim 1, wherein the combined triggering and cocking system is prevented from moving back to an original position after the triggering phase.

14. The lancet device of claim 1, wherein the combined triggering and cocking system is prevented from moving back to an original position after the cocking phase.

15. The lancet device of claim 1, wherein the combined triggering and cocking system is prevented from moving back to an original position after the cocking and triggering phases.

16. The lancet device of claim 1, wherein the lancet device has an adjustable depth of penetration arrangement.

17. The lancet device of claim 1, further comprising a front cover movably connected to one end of a body of the lancet device.

18. A lancet device comprising:
- a skin engaging surface that includes a lancet opening through which a lancet needle may extend;
- a lancet needle movable parallel to a central axis of the lancet opening;
- a spring that is compressed when the lancet needle moves from an original and/or intermediate position to a retracted position;
- a combined triggering and cocking system comprising one portion disposed outside the lancet device and another portion disposed inside the lancet device;
- the portion arranged outside being:
  - movable relative to a sidewall of the lancet device; and
  - closer to the skin engaging surface than the spring in the original position;
- the other portion being structured and arranged to cause movement of the lancet needle to the retracted position during a cocking phase and to allow the lancet needle to move to an extended position during a triggering phase,
- wherein, when a user moves the portion disposed outside, the other portion moves from one side of the central axis to another side of the central axis during at least the cocking phase, and
- wherein the lancet needle is movable back to the original position and/or intermediate position after triggering of the lancet device.

19. The lancet device of claim 18, further comprising a removable cap that when removed allows a user to install a lancet having the lancet needle.

20. A multi-use lancet device comprising:
- a skin engaging surface that includes a lancet opening through which a lancet needle may extend;
- a lancet needle movable parallel to a central axis of the lancet opening;
- a combined triggering and cocking system comprising two portions disposed outside the lancet device;
- each of the two portions arranged outside being movable relative to a sidewall of the lancet device;
- wherein, when a user moves the two portions disposed outside, the lancet needle first moves to a retracted position and then a triggering of the lancet device occurs whereby the lancet needle is automatically caused to move to a puncturing position, and
- wherein the lancet needle is movable back to an original position and/or intermediate position after triggering of the lancet device.

21. A multi-use lancet device comprising:
- a housing having a skin engaging end that includes a lancet opening through which a lancet needle may extend;
- a compression spring mounted within the housing;
- a movably mounted holding member configured to receive a replaceable lancet;
- a combined triggering and cocking system structured and arranged to move the holding member to a retracted position during a cocking phase and to cause the holding member to move to an extended position during a triggering phase; and
- a button portion of the combined triggering and cocking system being located outside the housing and being located closer to the skin engaging end than both the compression spring and the holding member.

\* \* \* \* \*